US007511156B2

(12) United States Patent
Corey

(10) Patent No.: US 7,511,156 B2
(45) Date of Patent: Mar. 31, 2009

(54) ANALOGS OF SALINOSPORAMIDE A

(75) Inventor: Elias J. Corey, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 11/539,648

(22) Filed: Oct. 9, 2006

(65) Prior Publication Data

US 2007/0161693 A1 Jul. 12, 2007

Related U.S. Application Data

(63) Continuation of application No. PCT/US2005/012113, filed on Apr. 11, 2005.

(60) Provisional application No. 60/560,877, filed on Apr. 9, 2004.

(51) Int. Cl.
*C07D 491/044* (2006.01)
(52) U.S. Cl. .................................................. 548/453
(58) Field of Classification Search .................. 548/453
See application file for complete search history.

(56) References Cited

U.S. PATENT DOCUMENTS

2004/0138196 A1 7/2004 Fenical et al.
2005/0203162 A1* 9/2005 Xiao et al. .................. 514/412

FOREIGN PATENT DOCUMENTS

| WO | 02094311 A1 | 11/2002 |
| WO | 2004071382 A2 | 2/2004 |
| WO | 2005002572 A2 | 1/2005 |

OTHER PUBLICATIONS

Corey et al., "Total Synthesis of Lactacystin," Journal of the American Chemical Society, vol. 114, pp. 10677-10678 (1992).
Corey et al., "An Efficient Total Synthesis of a New and Highly Active Analog of Lactacystin," Tetrahedron Letters, vol. 39, pp. 7475-7478 (1998).
Panek et al., "Total Synthesis of (+)-Lactacystin," Angewandte Chemie International Edition, vol. 38, pp. 1093-1095 (1999).
Soucy et al., "A Novel and Efficient Synthesys of a Highly Active Analogue of clasto-Lactacystin B-Lactone," Journal of the American Chemical Society, vol. 121, pp. 9967-9976 (1999).
Crane et al., "A Novel Enantioselective Synthetic Route to Omuralide Analogs with the Potential for Species Selectivity in Proteasome Inhibition," Organic Letters, vol. 3, pp. 1395-1397 (2001).
Saravanan et al., "A Short, Stereocontrolled, and Practical Synthesis of alpha-Methylomuralide, a Potent Inhibitor of Proteasome Function," Journal of Organic Chemistry, vol. 68, pp. 2760-2764 (2003).

* cited by examiner

*Primary Examiner*—Kamal A Saeed
*Assistant Examiner*—Jason Nolan

(57) ABSTRACT

Disclosed herein are analogs of Salinosporamide A, having the Formulae Ia-IVa as follows:

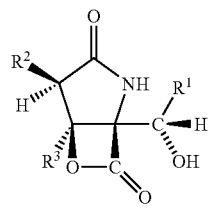

Ia

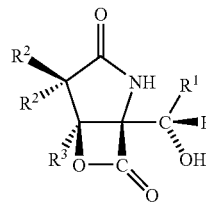

IIa

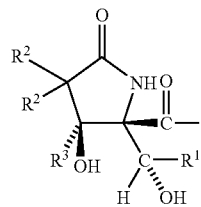

IIIa

Like Salinosporamide A, the compounds of the present invention will inhibit the proteasome, an intracellular enzyme complex that destroys proteins the cell no longer needs. Without the proteasome, proteins would build up and clog cellular machinery. Fast-growing cancer cells make especially heavy use of the proteasome, so thwarting its action is a compelling drug strategy.

7 Claims, 6 Drawing Sheets

Scheme 1

ANALOGS OF SALINOSPORAMIDE A

CROSS-REFERENCE TO RELATED APPLICATIONS

The present application is a continuation of PCT Application No. PCT/US2005/012113, filed Apr. 11, 2005, which designated the United States and was published in the English language on Oct. 27, 2005 as PCT Publication No. WO 2005/099687. The PCT Application claims priority from U.S. Provisional Patent Application Ser. No. 60/560,877, filed Apr. 9, 2004. These applications are hereby incorporated herein by reference.

BACKGROUND OF THE INVENTION

Salinosporamide A (1) was recently discovered by Fenical et al. as a bioactive product of a marine microorganism that is widely distributed in ocean sediments. See, Feeling et al., Angew. Chem. Int. Ed., 2003, 42, 355-357.

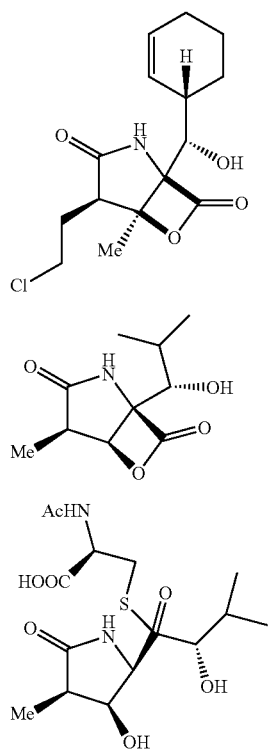

Structurally Salinosporamide A closely resembles the terrestrial microbial product Omuralide (2a) that was synthesized by Corey et al. several years ago and demonstrated to be a potent inhibitor of proteasome function. See, (a) Corey et al., Chem. Pharm. Bull., 1999, 47, 1-10; (b) Corey et al., Tetrahedron Lett., 1993, 34, 6977-6980; (c) Corey et al., J. Am. Chem. Soc., 1992, 114, 10677-10678; and (d) Fenteany et al., Proc. Natl. Acad. Sci. USA, 1994, 91, 3358-3362.

A simple and effective stereocontrolled synthesis of Salinosporamide A is taught in commonly owned, copending U.S. patent application Ser. No. 10/821,621, filed 9 Apr. 2004. The process described therein is capable of providing Salinosporamide A, and with minor modifications, is likewise capable of providing compounds of the present invention. The relevant portions of that disclosure are presented below.

Like Omuralide, Salinosporamide A inhibits the proteasome, an intracellular enzyme complex that destroys proteins the cell no longer needs. Without the proteasome, proteins would build up and clog cellular machinery. Fast-growing cancer cells make especially heavy use of the proteasome, so thwarting its action is a compelling drug strategy. See, Fenical et al., U.S. Patent Publication No. 2003-0157695A1, the disclosure of which is hereby incorporated herein by reference.

Omuralide is generated by β-lactonization of the N-acetyl-cysteine thiolester lactacystin (2b) that was first isolated by the Omura group as a result of microbial screening for nerve growth factor-like activity. See, Omura et al., J. Antibiot., 1991, 44, 113-116; and Omura et al., J. Antibiot., 1991, 44, 117-118.

Methods for preparing lactacystin and related compounds, including analogs of lactacystin and clasto-lactacystin beta-lactone, are taught in the following references; U.S. Pat. Nos. 6,645,999; 6,566,553; 6,458,825; 6,335,358; 6,294,560; 6,214,862; 6,147,223; 6,133,308; 5,869,675; 5,756,764; and PCT Publication No. WO 96/32105; the disclosures of which are hereby incorporated herein by reference. See also, (a) Corey et al., Total Synthesis of Lactacystin, J. Am. Chem. Soc., 1992, 114, 10677-10678; (b) Corey et al., An Enantioselective Synthesis of (6R)-Lactacystin, Tetrahedron Lett., 1993, 34, 6969-6972; (c) Corey et al., Synthesis of (6R, 7S)-Lactacystin and 6-Deoxy-lactacystin from a Common Intermediate, Tetrahedron Lett., 1993, 34, 6973-6975; and (d) Corey et al., Total Synthesis of Lactacystin: An Enantioselective Synthesis of (6R)-Lactacystin: Total Synthesis of (+)-Lactacystin, . . . , Chemtracts-Organic Chemistry, pp. 266-272, 1994.

SUMMARY OF THE INVENTION

One embodiment of the present invention provides compounds having the Formula Ia:

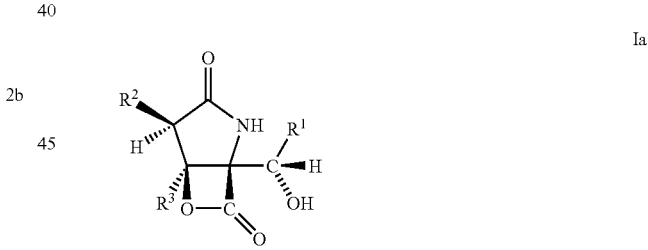

wherein:
$R^1$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, and halogen;
$R^2$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, halogen and aryl;
$R^3$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, methylene-C3-C8 cycloalkyl, benzyl and substituted benzyl; wherein the substituent groups are independently selected from the group consisting of C1-C4 alkoxy, amido, and halogen; and with the proviso that $R^3$ is not methyl when $R^2$ is 2-chloroethyl and $R^1$ is 2-cyclohexenyl.

In Formula Ia, $R^1$ is preferably selected from the group consisting of methyl, ethyl, propyl, iso-propyl, n-butyl, iso-butyl, and tert-butyl, each optionally substituted by halogen, preferably selected from Cl and F.

Alternatively, in Formula Ia, $R^1$ is preferably selected from the group consisting of cyclopropyl, cyclobutyl, cyclopentyl and cyclohexyl, each optionally with a double bond.

In Formula Ia, $R^2$ is preferably selected from the group consisting of methyl, ethyl, n-propyl, iso-propyl, n-butyl, iso-butyl and tert-butyl, each optionally substituted by one or more substituents selected from the group consisting of C1-C4 alkoxy, amido, halogen and aryl. Preferred halogens are Cl and F.

In Formula Ia, $R^3$ is preferably selected from the group consisting of methyl, ethyl, n-propyl, iso-propyl, n-butyl, iso-butyl, and tert-butyl, each optionally substituted with a substituent selected from the group consisting of halogen and C1-C4 alkoxy. Preferred halogens are Cl and F.

Another embodiment of the present invention is compounds having the Formula IIa:

IIa wherein:
$R^1$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, and halogen;

Each $R^2$ group is independently selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, halogen and aryl; or Alternatively, the two $R^2$ groups are joined to form the spiro ring group:

—CH$_2$—(CH$_2$)$_n$—CH$_2$— where n has a value selected from 0, 1, 2, 3, or 4; and $R^3$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, methylene-C3-C8 cycloalkyl, benzyl and substituted benzyl; wherein the substituent groups are independently selected from the group consisting of C1-C4 alkoxy, amido, and halogen.

In Formula IIa, $R^1$ is preferably selected from the group consisting of methyl, ethyl, propyl, iso-propyl, n-butyl, iso-butyl, and tert-butyl, each optionally substituted by halogen, preferably selected from Cl and F.

Alternatively, in Formula IIa, $R^1$ is preferably selected from the group consisting of cyclopropyl, cyclobutyl, cyclopentyl and cyclohexyl, each optionally with a double bond.

In Formula IIa, each $R^2$ is preferably selected from the group consisting of methyl, ethyl, n-propyl, iso-propyl, n-butyl, iso-butyl and tert-butyl, each optionally substituted by one or more substituents selected from the group consisting of C1-C4 alkoxy, amido, halogen and aryl. Preferred halogens are Cl and F.

Alternatively, in Formula IIa, two $R^2$ groups together preferably form a sprio cyclopropyl, cyclobutyl, cyclopentyl or cyclohexyl group.

In Formula IIa, $R^3$ is preferably selected from the group consisting of methyl, ethyl, n-propyl, iso-propyl, n-butyl, iso-butyl, and tert-butyl, each optionally substituted with a substituent selected from the group consisting of halogen and C1-C4 alkoxy. Preferred halogens are Cl and F.

Another embodiment of the present invention is compounds having the Formula IIIa:

IIIa wherein:
$R^1$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, and halogen;

Each $R^2$ group is independently selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, and halogen;

Alternatively, the two $R^2$ groups are joined to form the spiro ring group:

—CH$_2$—(CH$_2$)$_n$—CH$_2$— where n has a value selected from 0, 1, 2, 3, or 4; and

Alternatively, one $R^2$ group can be H;

$R^3$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, methylene-C3-C8 cycloalkyl, benzyl and substituted benzyl; wherein the substituent groups are independently selected from the group consisting of C1-C4 alkoxy, amido, and halogen; and X is an ester or thoiester precursor of the beta-lactone. These ester compounds may serve as prodrugs for the desired beta-lactone compounds. An especially preferred X group has the formula:

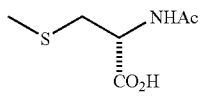

In Formula IIIa, $R^1$ is preferably selected from the group consisting of methyl, ethyl, propyl, iso-propyl, n-butyl, iso-butyl, and tert-butyl, each optionally substituted by halogen, preferably selected from Cl and F.

Alternatively, in Formula IIIa, $R^1$ is preferably selected from the group consisting of cyclopropyl, cyclobutyl, cyclopentyl and cyclohexyl, each optionally with a double bond.

In Formula IIIa, each $R^2$ is preferably independently selected from the group consisting of methyl, ethyl, n-propyl, iso-propyl, n-butyl, iso-butyl and tert-butyl, each optionally substituted by one or more substituents selected from the group consisting of $C_1$-$C_4$ alkoxy, amido, halogen and aryl. Preferred halogens are Cl and F.

In Formula IIIa, $R^3$ is preferably selected from the group consisting of methyl, ethyl, n-propyl, iso-propyl, n-butyl, iso-butyl, and tert-butyl, each optionally substituted with a substituent selected from the group consisting of halogen and C1-C4 alkoxy. Preferred halogens are Cl and F.

The compounds of the present invention are expected to possess the same range of activities exhibited by Salinosporamide A and the other related compounds discussed above, namely omuralide, lactacystin and the known analogs of lactacystin and clasto-lactacystin beta-lactone. See, Masse et al., Eur. J. Org. Chem., 2000, 2513-2528.

DETAILED DESCRIPTION OF THE INVENTION

Figures 1, 1A:
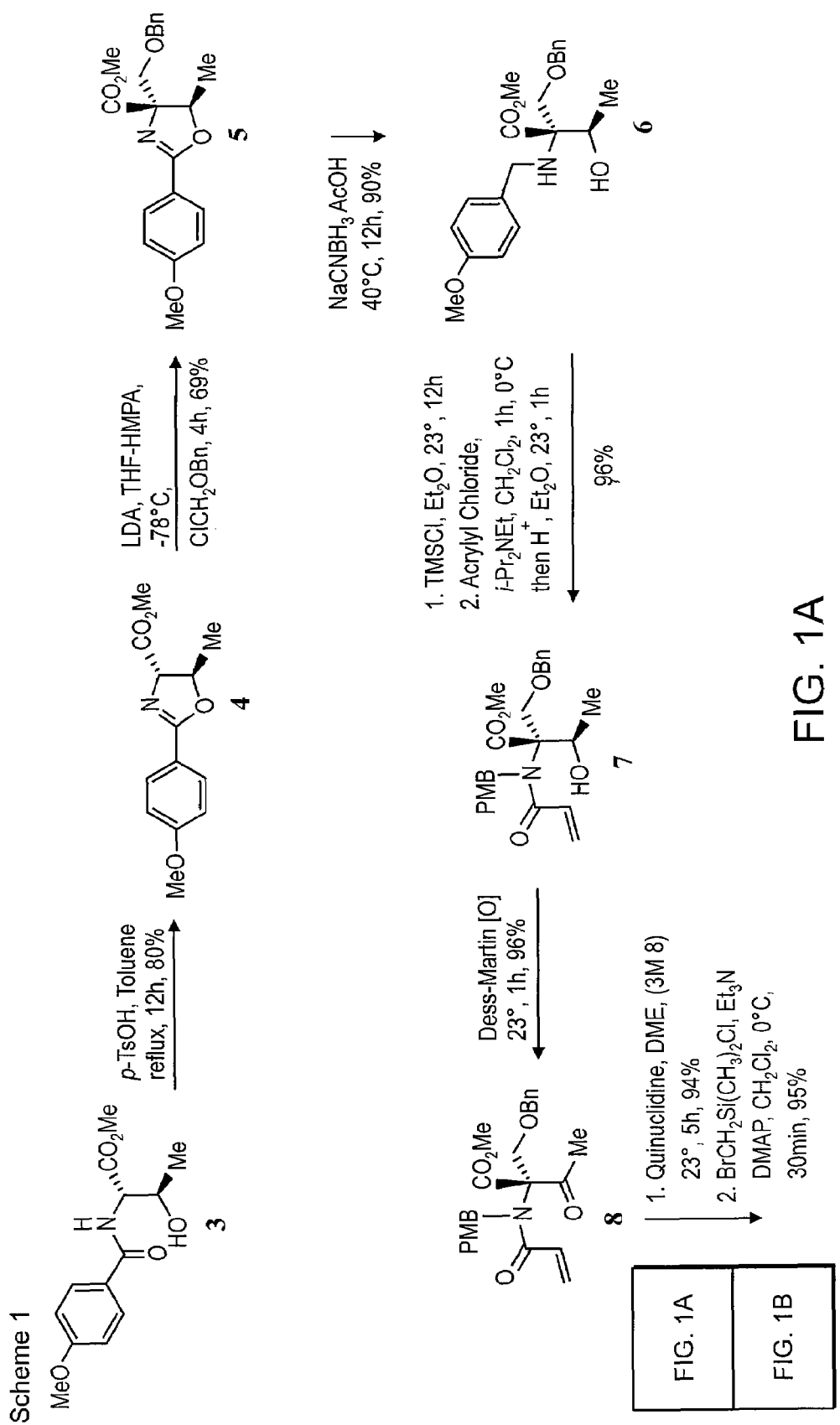
FIG. 1 shows a synthetic scheme (Scheme 1) useful in the formation of the compounds of the present invention.
Figure 1B:
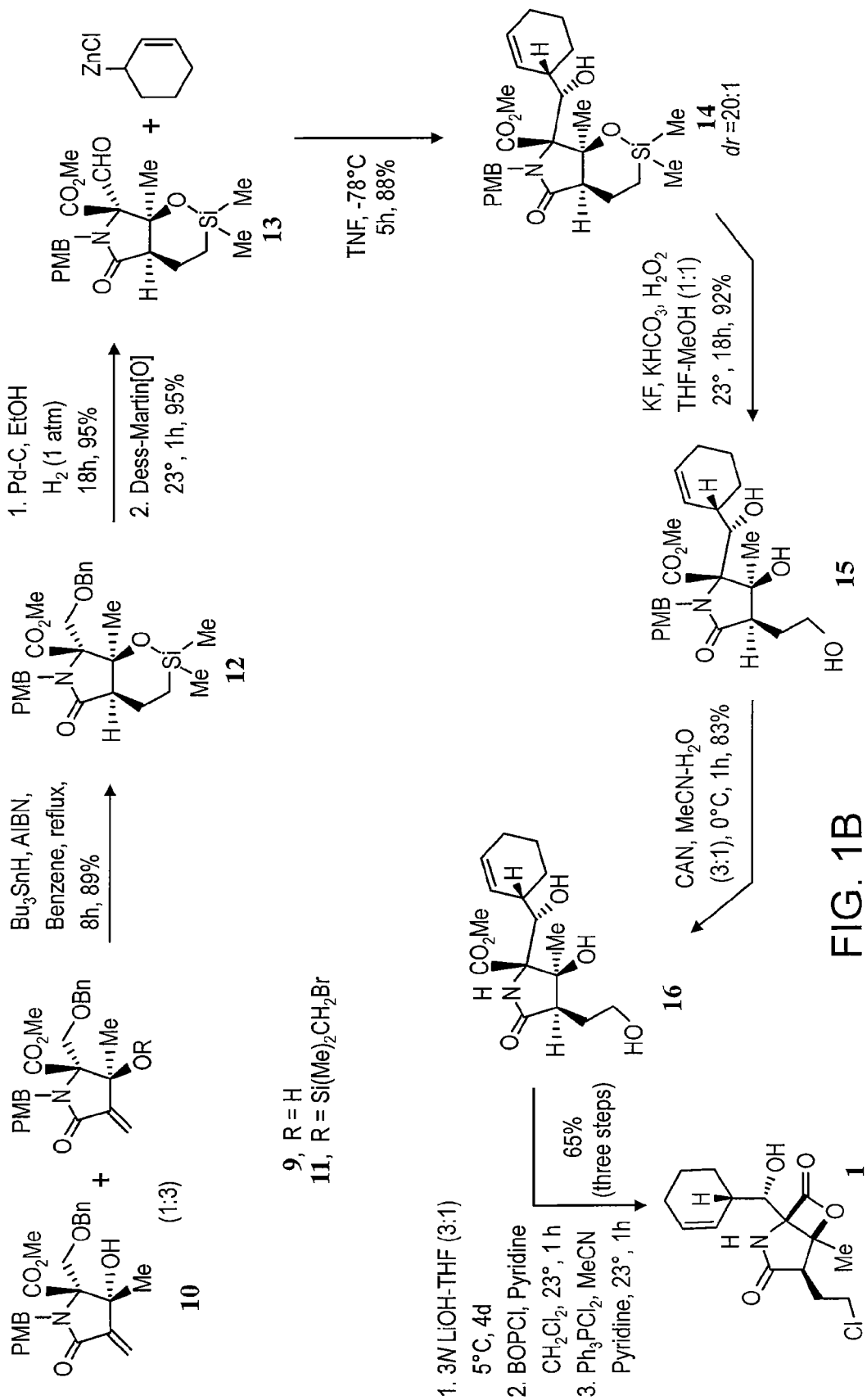
Figure 2A:
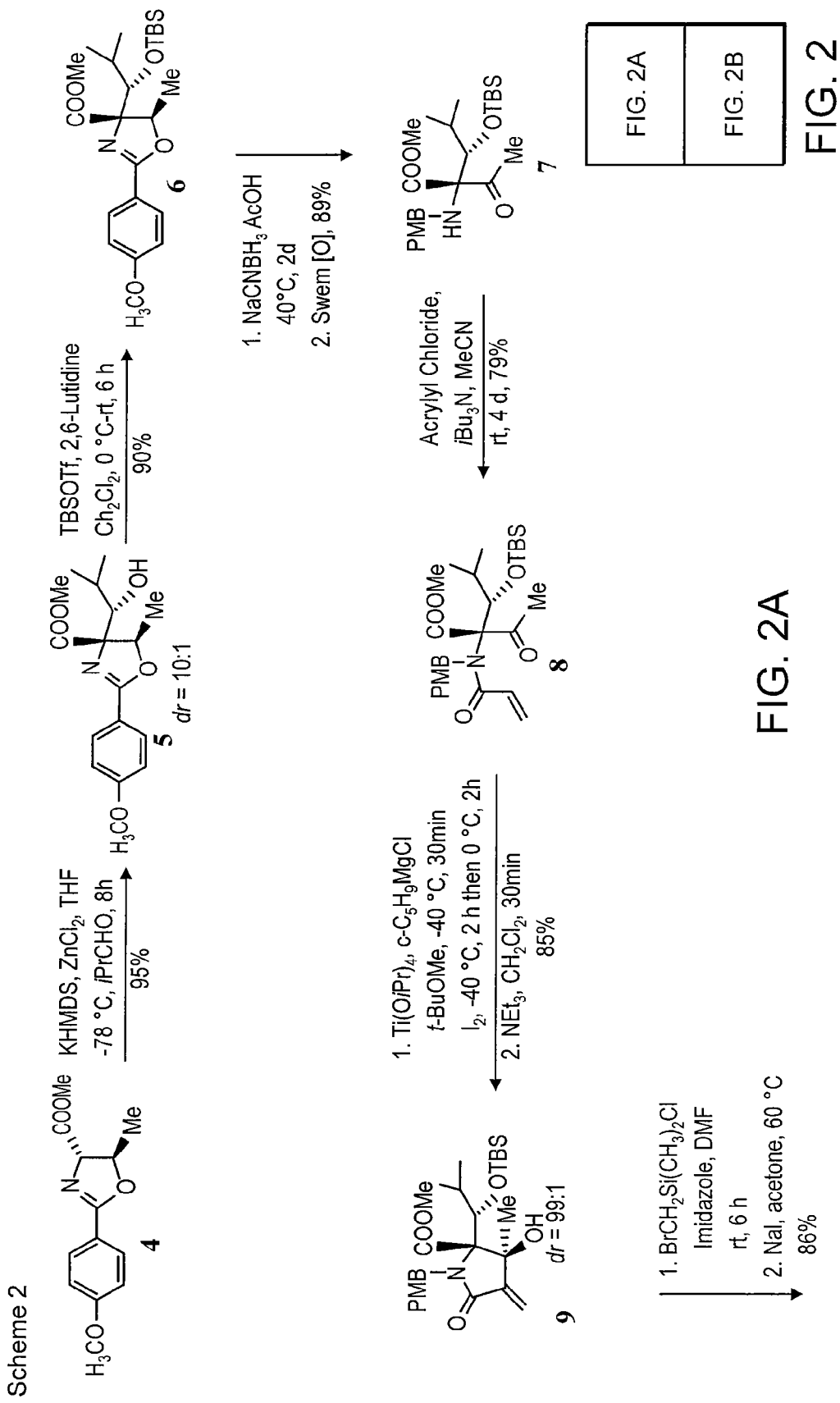
FIG. 2 shows another synthetic scheme (Scheme 2) useful in the formation of the compounds of the present invention.
Figure 2B:
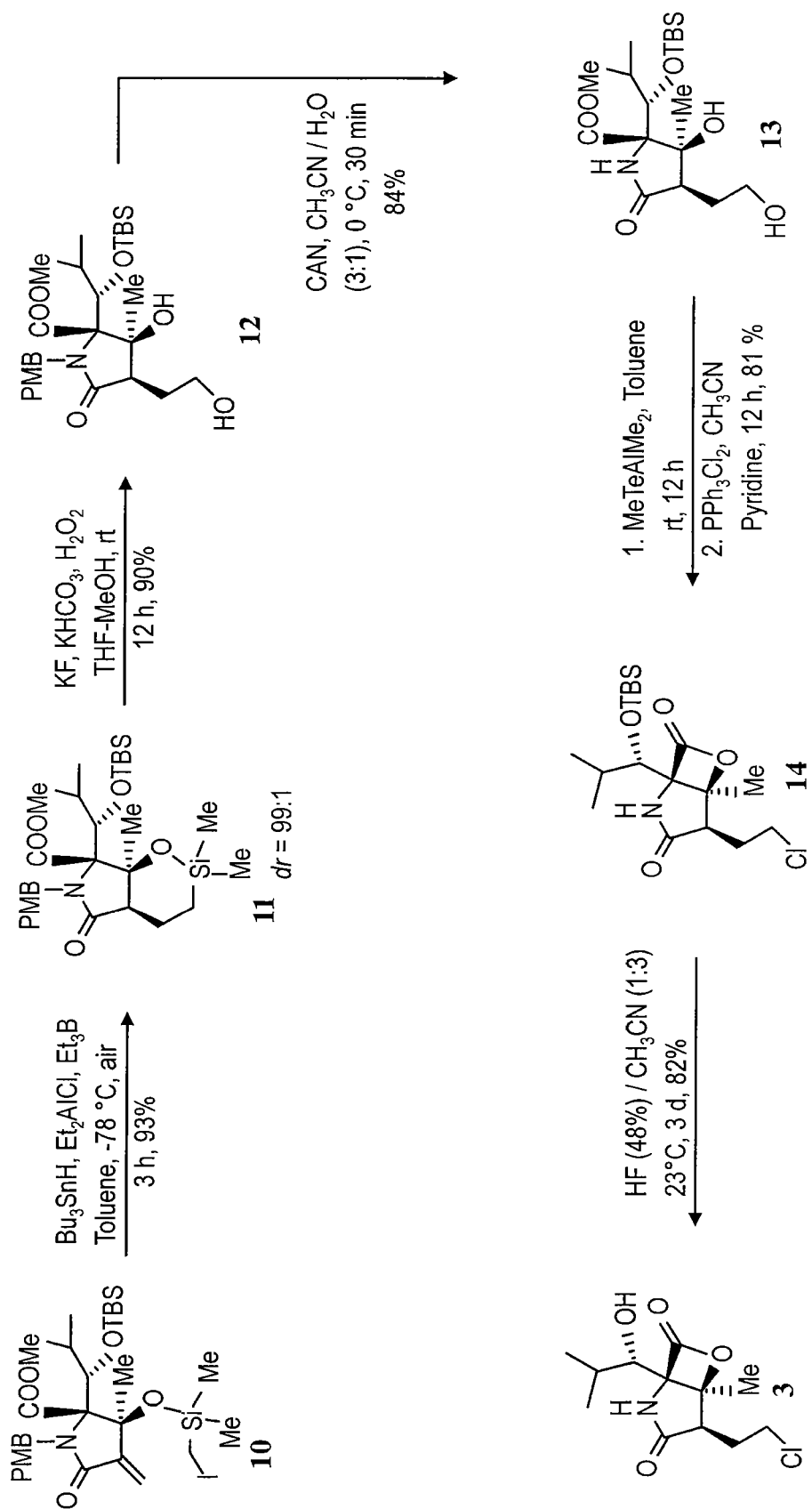
Figure 3A:
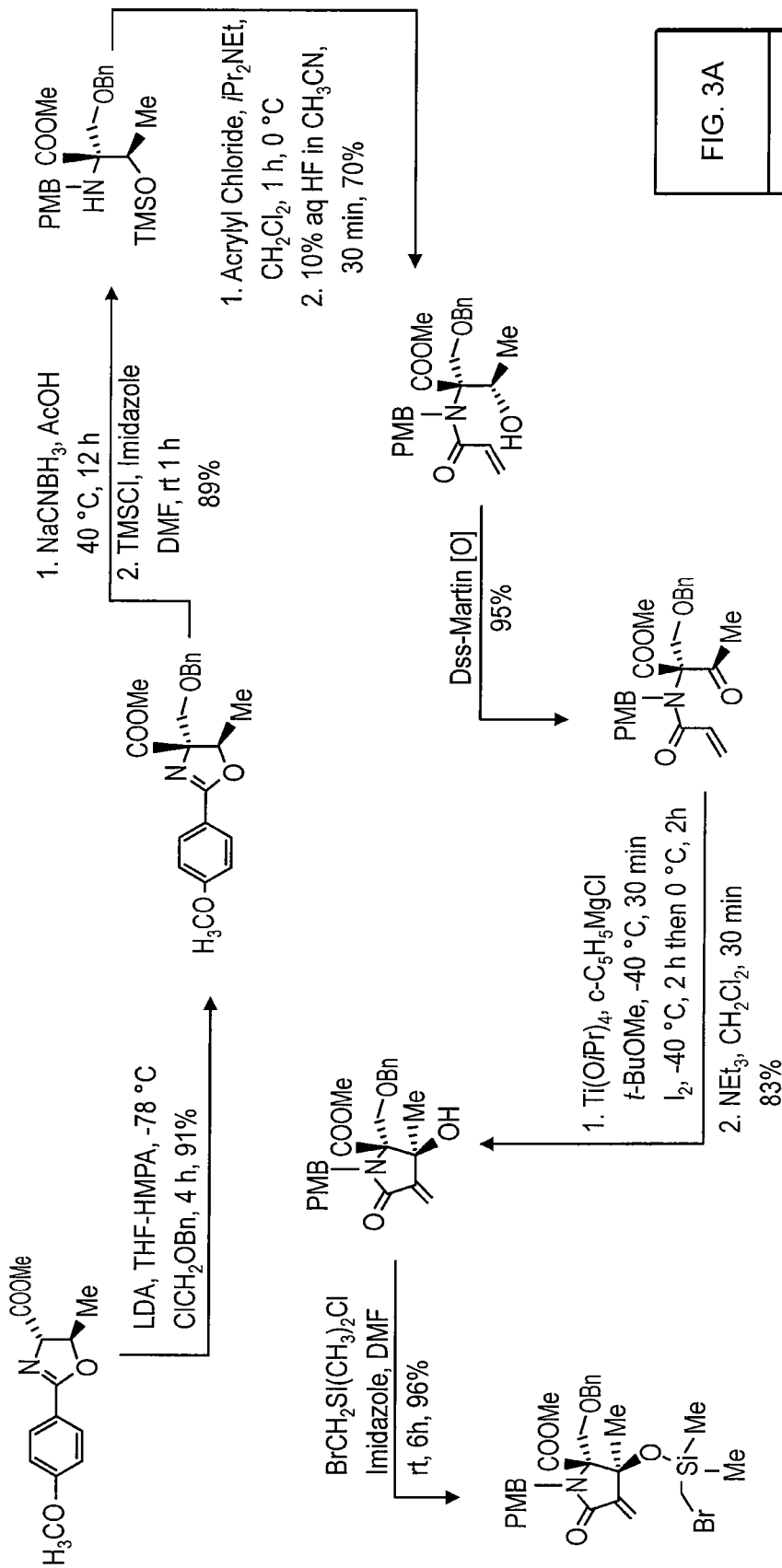
FIG. 3 shows another synthetic scheme (Scheme 3) useful in the formation of the compounds of the present invention.
Figure 3B:
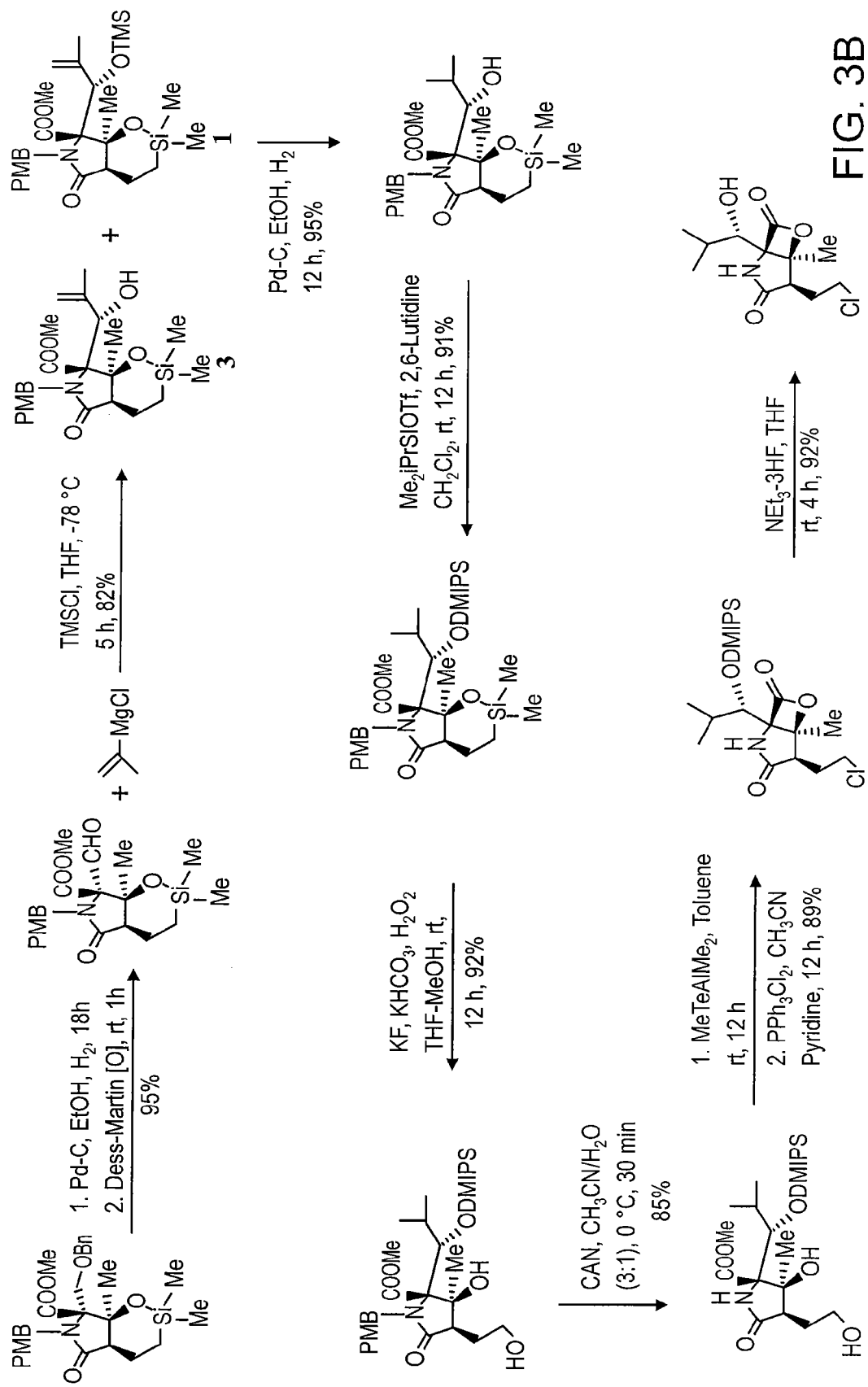

Retrosynthetic analysis may be employed by the skilled artisan to devise alternate synthetic routes to the compounds of the present invention. See, Corey et al., "The Logic of Chemical Synthesis," ISBN 0-471-11594-0, published by John Wiley & Sons (1995).

In Scheme 1, the compound of Formula 3 is utilized as the starting material for preparation of compounds of Formula Ia wherein $R^3$ is methyl. One of ordinary skill in the art will appreciate that compounds of Formula Ia-IIIa wherein $R^3$ is other than methyl can be analogously prepared from starting materials wherein the methyl group is replaced by the appropriate $R^3$ group.

In Schemes 2 and 3, two preparations of compounds of Formula Ia wherein $R^3$ is isopropyl are shown. One of ordinary skill in the art will appreciate that compounds of Formula Ia-IIIa wherein $R^3$ is other than isopropyl can be analogously prepared from starting materials wherein the isopropyl group is replaced by another desired $R^3$ group.

Scheme 1:

Compound 3 can be cyclized to the oxazoline 4 by heating at reflux in toluene with p-toluenesulfonic acid:

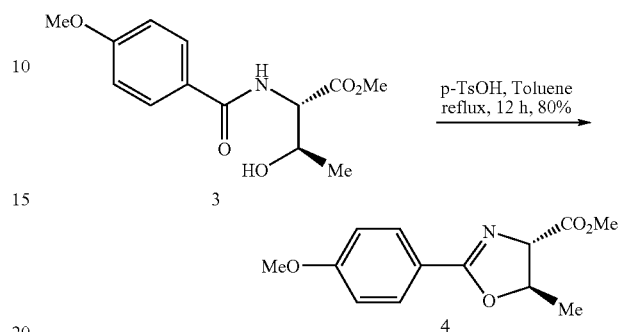

Deprotonation of 4 with lithium diisopropylamide in THF and alkylation of the resulting enolate with chloromethyl benzyl ether will afford the desired tertiary stereocenter of formula 5:

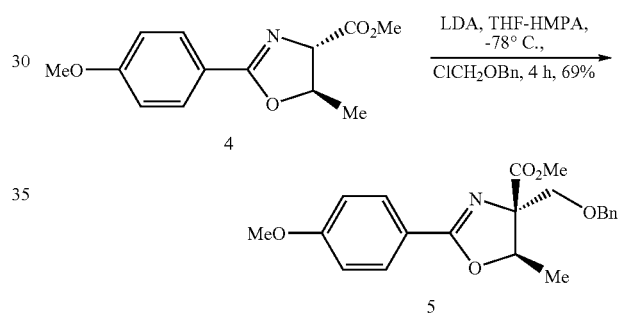

Reduction of 5 with $NaBH_3CN$—HOAc will give the N-4-methoxybenzylamine 6:

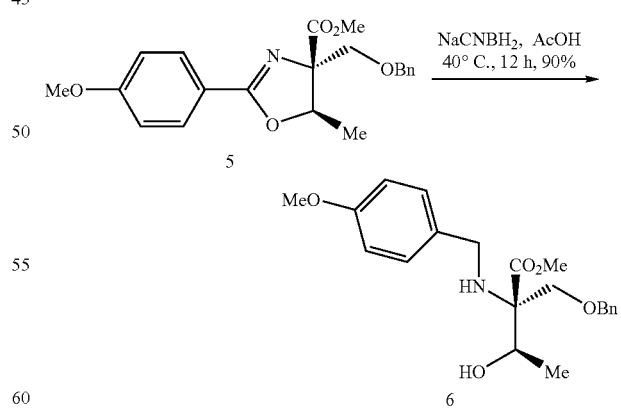

Compound 6 can be transformed to the N-acrylyl-N-4-methoxybenzyl derivative 7 by (1) reaction with $Me_3SiCl$ and $Et_3N$ to form the TMS ether (6a OH is OTMS), followed by (2) acylation with acrylyl chloride at 0° C. and (3) acidic work up with aqueous HCl:

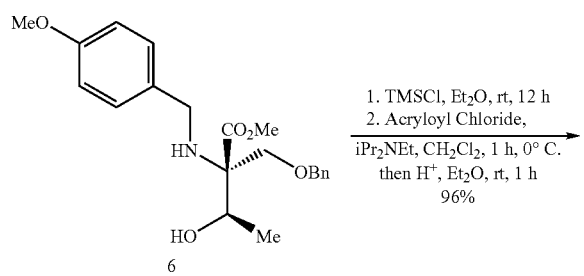

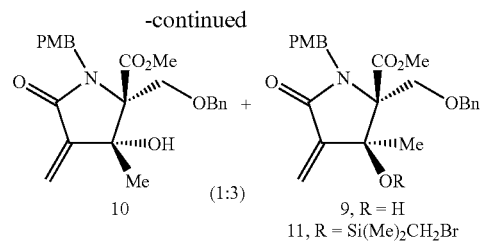

Silylation of 9 with bromomethyldimethylsilyl chloride will afford 11 (where PMB=4-methoxybenzyl). Silyl ether 11 and the diastereomeric silyl ether can then be separated, e.g., by silica gel column chromatography.

The desired stereochemical relationship about C(α) and C(β) of the γ-lactam core can be formed by tri-n-butyltin hydride-mediated radical-chain cyclization which will transform 11 into the cis-fused γ-lactam 12 (where PMB=4-methoxybenzyl):

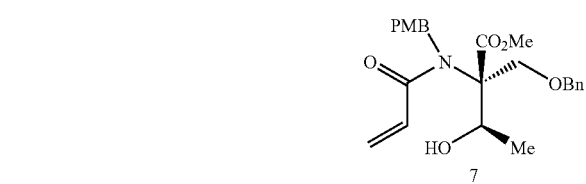

Dess-Martin periodinane oxidation of 7 will produce the keto amide ester 8 (where PMB=4-methoxybenzyl):

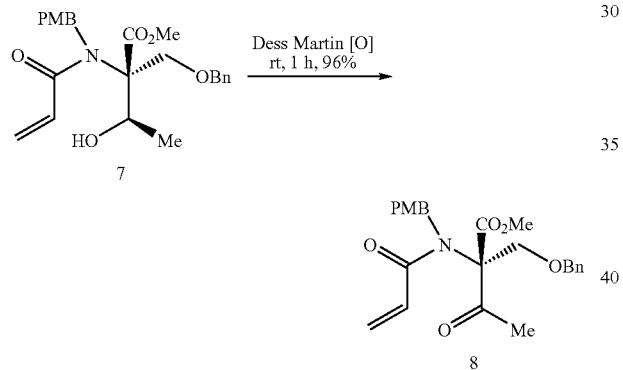

Cyclization of 8 to the γ-lactam 9 (where PMB=4-methoxybenzyl) can be accomplished by means of an internal Baylis-Hillman-aldol reaction using quinuclidine as the catalytic base in dimethoxyethane. See, Frank, S. A.; Mergott, D. J.; Roush, W. R., J. Am. Chem. Soc., 2002, 124, 2404-2405. Mergott, D. J.; Frank, S. A.; Roush, W. R., Org. Lett., 2002, 4, 3157-3160. Aggarwal, V. K.; Emme, I.; Fulford, S. Y., J. Org. Chem., 2003, 68, 692-700. Yeo, J. E.; Yang, X.; Kim, H. J.; Koo, S., J. Chem. Soc., Chem. Commun., 2004, 236-237. The cyclization products will consist of 9 and the C(β) diastereomer (10):

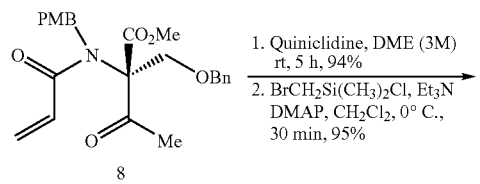

See, (a) Bols, M. Skrydstrup, T., Chem. Rev., 1995, 95, 1253-1277. (b) Fleming, I.; Barbero, A.; Walter, D., Chem. Rev., 1997, 97, 2063-2092. (c) Stork, G.; Mook, R.; Biller, S. A.; Rychnovsky, S. D., J. Am. Chem. Soc., 1983, 105, 3741-3742. (d) Stork, G.; Sher, P. M.; Chen, H. L., J. Am. Chem. Soc., 1986, 108, 6384-6385.

Cleavage of the benzyl ether of 12 ($H_2$, Pd—C) will yield the primary alcohol (12a —OBn is OH), and Dess-Martin periodinane oxidation of 12a will provide the aldehyde 13 (where PMB=4-methoxybenzyl):

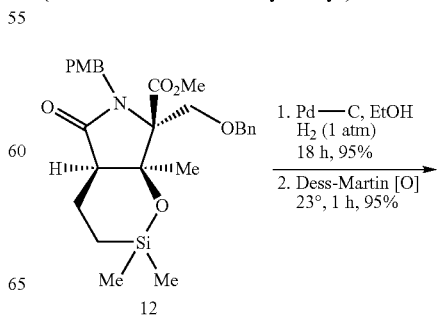

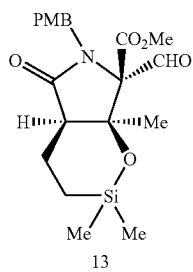

13

The next step, the attachment of the $R^1$ group to the formyl carbon and the establishment of the remaining two stereocenters may be accomplished as follows. A compound having the formula $R^1$—ZnCl may be formed, for example as follows (where $R^1$ is 2-cyclohexenyl):

2-Cyclohexenyl-tri-n-butyltin (from Pd(0)-catalyzed 1,4-addition of tributyltin hydride to 1,3-cyclohexadiene) is sequentially transmetalated by treatment with 1 equiv of n-butyllithium and 1 equiv of zinc chloride to form 2-cyclohexenylzinc chloride in THF solution. See, Miyake, H.; Yamamura, K. Chem. Lett. 1992, 507-508. Reaction of this reagent with the aldehyde 13 will yield the desired formyl adduct 14 stereoselectively:

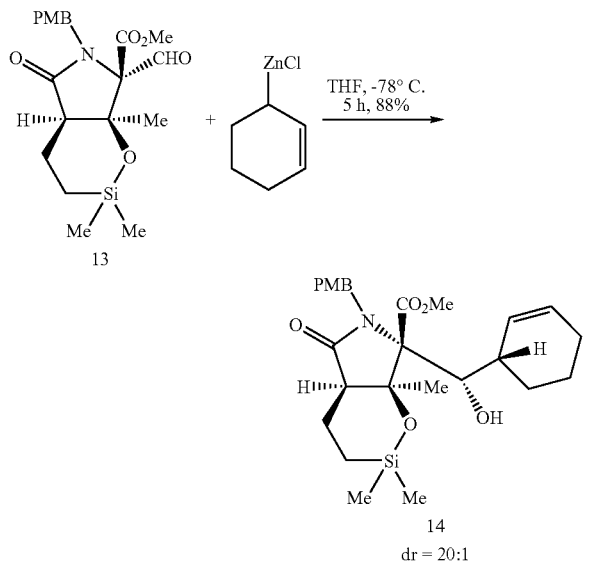

Tamao-Fleming oxidation of 14 will provide the triol 15:

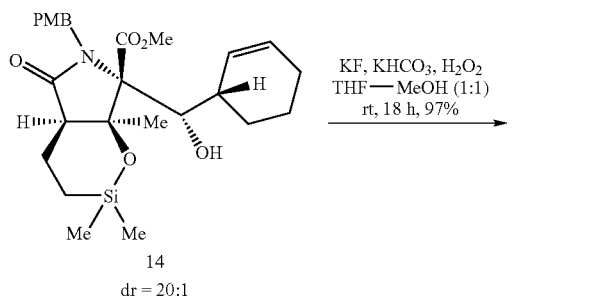

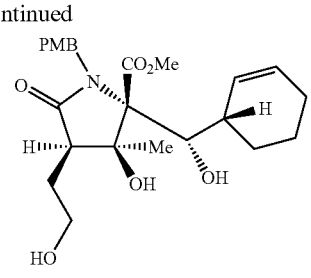

15

See, Fleming, T., Chemtracts-Org. Chem., 1996, 9, 1-64, and Jones, G. R.; Landais, Y., Tetrahedron, 1996, 52, 7599-7662.

Ce(IV)-induced oxidative cleavage of the PMB group of 15 will afford the triol ester 16:

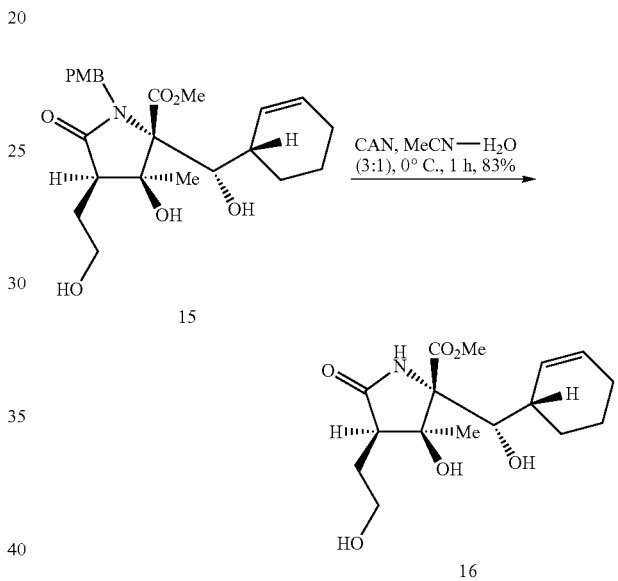

Compound 16 can then be hydrolyzed to the corresponding γ-lactam-carboxylic acid 16a ($CO_2Me$ is $CO_2H$) using 3:1 aqueous 3N-lithium hydroxide and THF at 4° C.

The acid 16a can then be cyclized to the beta-lactone, i.e., Formula Ia where $R^1$ is 2-cyclohexenyl, $R^2$ is $CH_2CH_2OH$, and $R^3$ is methyl. The compound of Formula Ia can then be further modified if desired, e.g., to vary the group at R. Compounds of Formula IIa can be formed by using known techniques to form the spiro compounds. Compounds of Formula IIIa can be formed by opening the beta-lactone ring using known techniques followed by appropriate esterification.

Scheme 2:

Step 1:

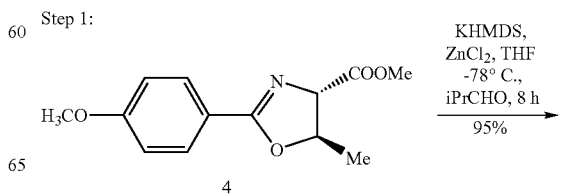

-continued

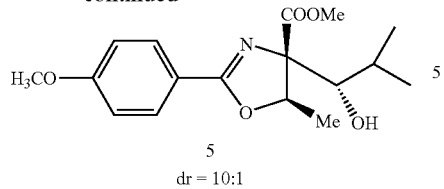

5
dr = 10:1

In this scheme, the R3 group (here R3=isopropyl) is introduced in the first step, in which isopropaldehyde, zinc chloride and potassium hexamethyldisilazane are reacted with Compound 4 to afford Compound 5.

Step 2:

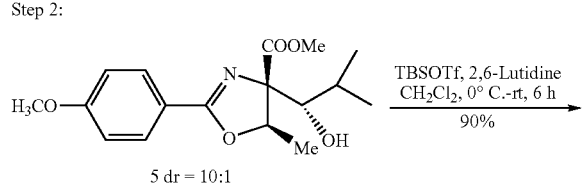

TBSOTf, 2,6-Lutidine
CH$_2$Cl$_2$, 0° C.-rt, 6 h
90%

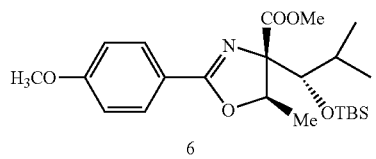

In Step 2, the hydroxyl group on Compound 5 is protected with t-butyldimethylsilyl triflate (TBSOTf) to afford Compound 6.

Step 3:

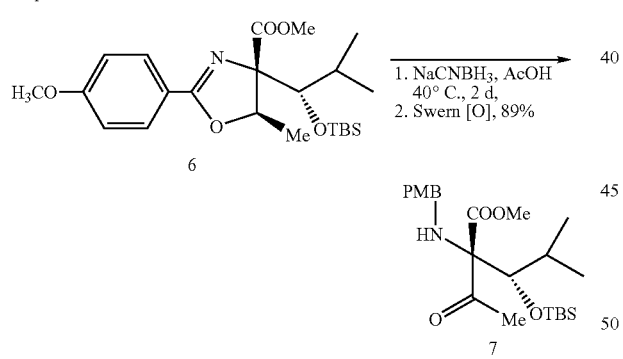

1. NaCNBH$_3$, AcOH
40° C., 2 d,
2. Swern [O], 89%

In Step 3, Compound 6 is first reacted with sodium cyanoborohydride, and then subjected to Swern oxidation to afford Compound 7.

Step 4:

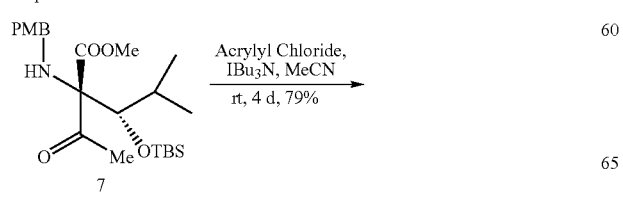

Acrylyl Chloride,
IBu$_3$N, MeCN
rt, 4 d, 79%

-continued

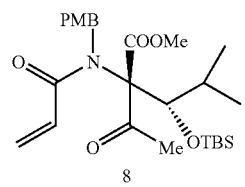

8

In Step 4, the amino group in Compound 7 is reacted with acrylyl chloride to form the amide of Compound 8.

Step 5:

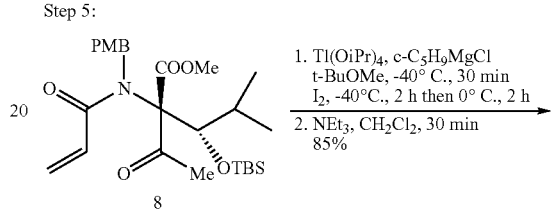

1. Tl(OiPr)$_4$, c-C$_5$H$_9$MgCl
t-BuOMe, -40° C., 30 min
I$_2$, -40°C., 2 h then 0° C., 2 h
2. NEt$_3$, CH$_2$Cl$_2$, 30 min
85%

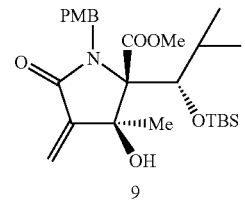

9
dr = 99:1

In Step 5, Compound 8, in a two-step procedure, is cyclized to form the substituted pyrrole—Compound 9.

Step 6:

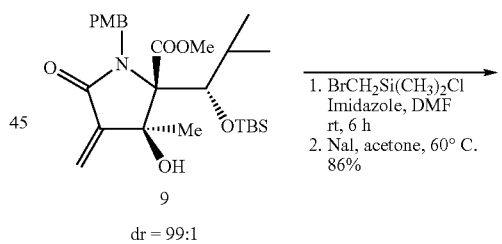

1. BrCH$_2$Si(CH$_3$)$_2$Cl
Imidazole, DMF
rt, 6 h
2. NaI, acetone, 60° C.
86%

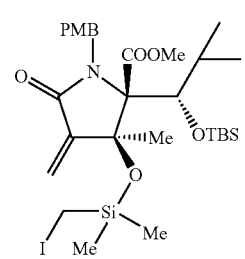

10

In Step 6, the free hydroxyl group in Compound 9, in a two-step procedure, is reacted with (bromomethyl)dimethylsilylchloride and sodium iodide, to form Compound 10, where the hydroxyl group is protected with (iodomethyl)dimethylsilane.

Step 7:

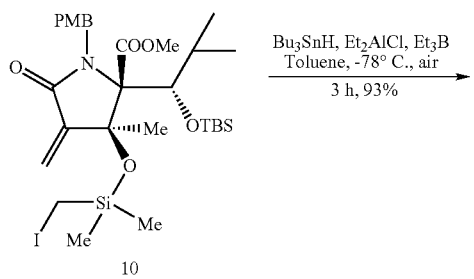

In Step 7, Compound 10 is cyclized to form Compound 11 using tributylstannane, diethylaluminum chloride and triethylborane.

Step 8:

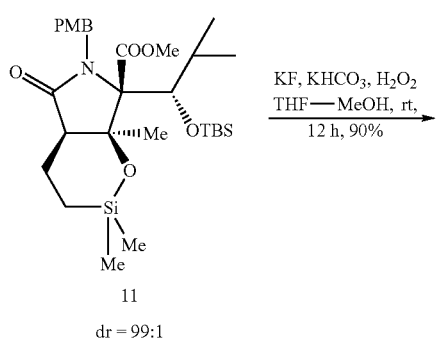

In Step 8, Compound 11 is oxidized in the presence of potassium fluoride, potassium bicarbonate and hydrogen peroxide, to afford Compound 12.

Step 9:

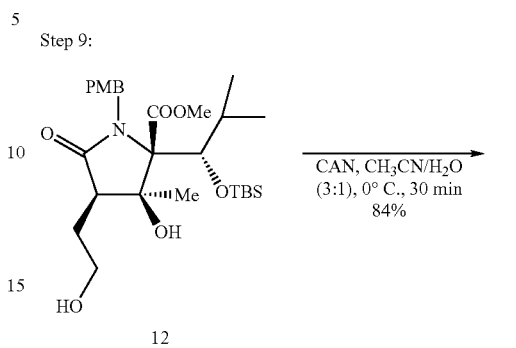

In Step 9, oxidative removal of the PMB protecting group in Compound 12 is accomplished with ceric (IV) ammonium nitrate (CAN) to afford Compound 13.

Step 10:

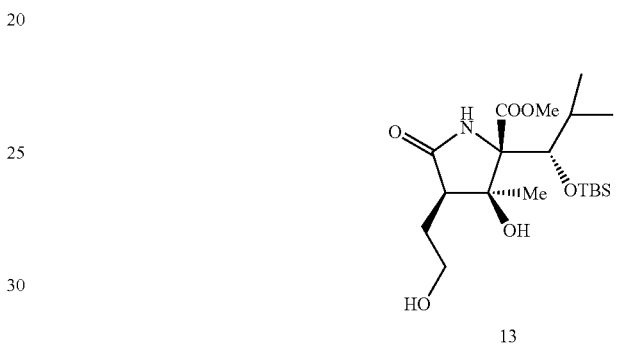

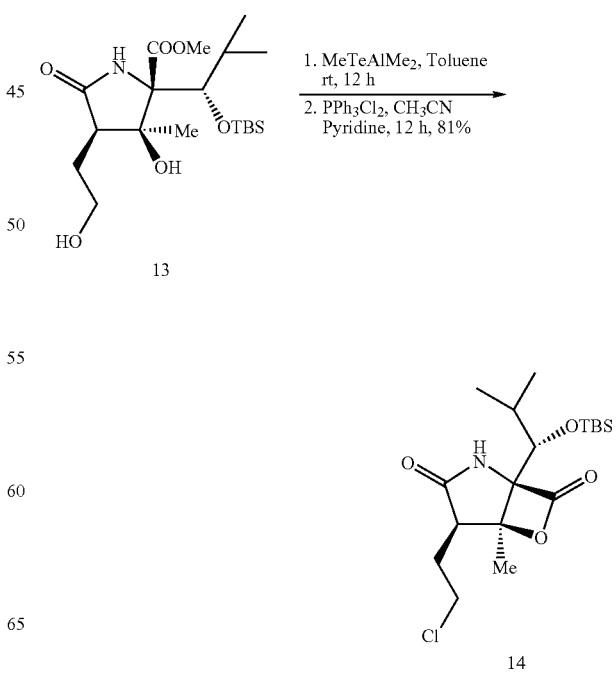

In Step 10, the methyl ester—Compound 13, in a two-step procedure, is converted into the beta-lactone—Compound 14, first by reaction with dimethylaluminum methyl tellurolate, followed by triphenylphosphine chloride.

Step 11:

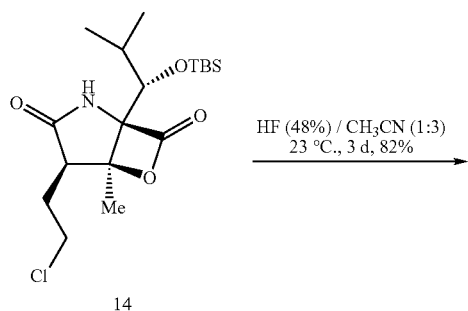

In Step 11, the TBS protecting group is removed using hydrogen fluoride to afford Compound 3.

Scheme 3:

In Scheme 3, the R³ group is introduced later in the synthetic sequence than in Scheme 2. In fact, Scheme 3 essentially repeats six steps of Scheme 1, starting with Compound 4 of that Scheme. As in Scheme 2, the end product has R³ as isopropyl, but as with the previous schemes, the skilled artisan can readily modify the reactants as required to introduce other substituents.

Step 1:

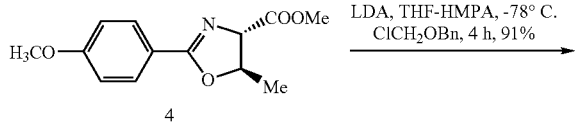

In Step 1, Compound 4 (from Scheme 2) is converted to Compound 15 by reaction with lithium diisopropyl amide and chloromethyl benzyl ether.

Step 2:

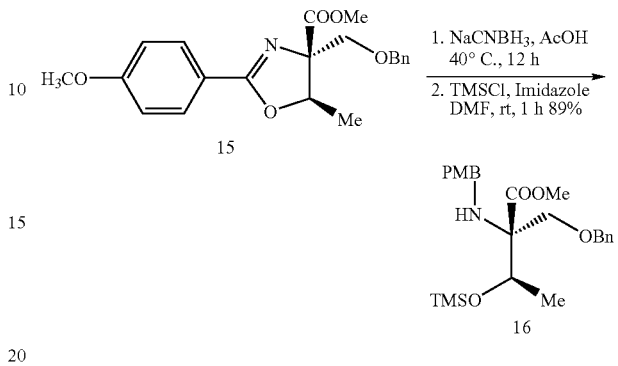

In Step 2, Compound 15 is converted, in a two-step procedure, to Compound 16—first by reaction with sodium cyanoborohydride and second by reaction with trimethylsilyl chloride.

Step 3:

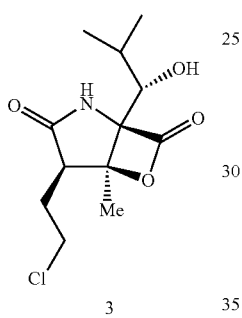

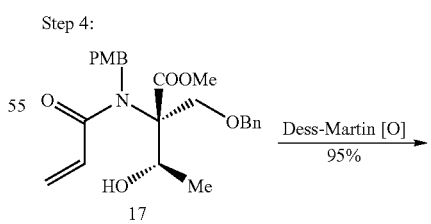

In Step 3, Compound 16 is converted, in a two-step procedure, to Compound 17—first by reaction with acrylyl chloride, and second by treatment with aqueous hydrogen fluoride.

Step 4:

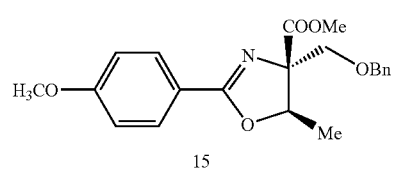

In Step 4, Compound 17 is subjected to Dess-Martin oxidation to afford Compound 18.

Step 5:

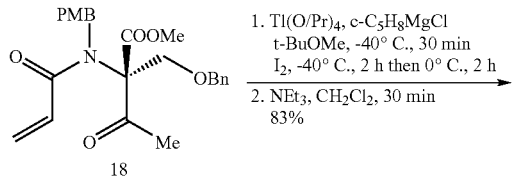

In Step 5, Compound 18, in a two-step procedure, is converted into the pyrrole, Compound 19—first by reaction with tetraisopropyl titanate, cyclopentyl magnesium chloride and tert-butyl methyl ether; followed by triethylamine.

Step 6:

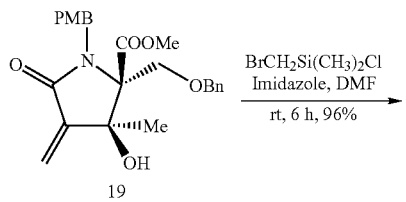

In Step 6, the free-hydroxyl group in Compound 19 is protected by reaction with bromomethyl dimethyl silylchloride and imidazole.

Step 7:

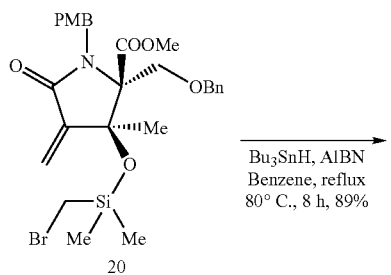

In Step 7, Compound 20 is reacted with tributylstannane and azoisobutyronitrile (AIBN) to afford the bicyclic compound 21.

Step 8:

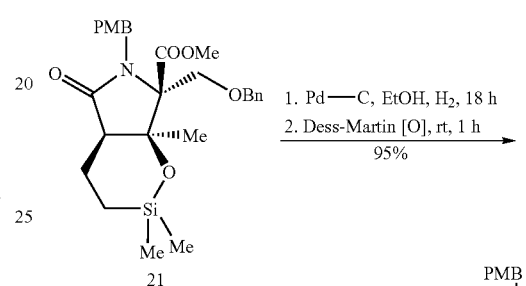

In Step 8, Compound 21 is converted, in a two-step procedure, to Compound 22—first by hydrogenation over Pd—C catalyst, followed by Dess-Martin oxidation.

Step 9:

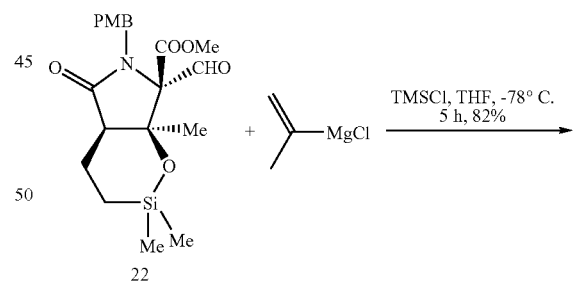

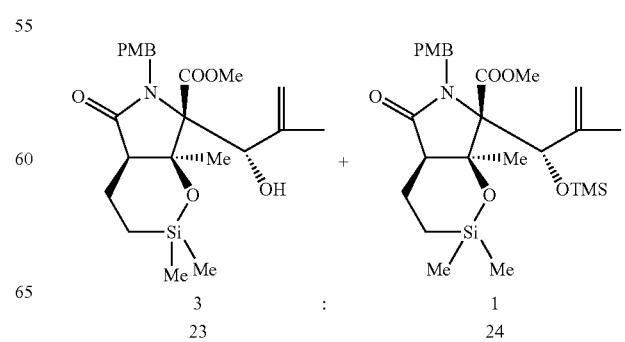

In Step 9, Compound 22 is reacted with the R3 precursor compound—in this case isopropenyl magnesium chloride—and trimethylsilyl chloride to afford a mixture of Compounds 23 and 24 in a 3:1 ratio.

Step 10:

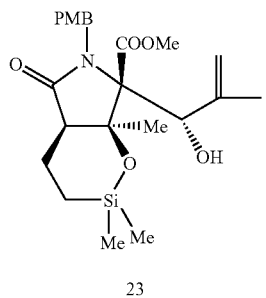

23

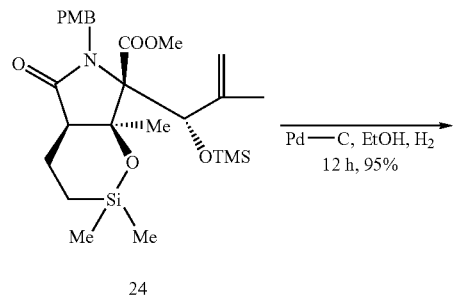

24

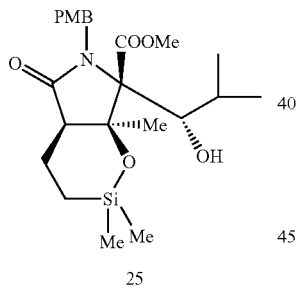

25

Hydrogenation of the mixture of Compounds 23 and 24 over Pd—C catalyst converts the mixture to Compound 25 in which R3 is now present as isopropyl.

Step 11:

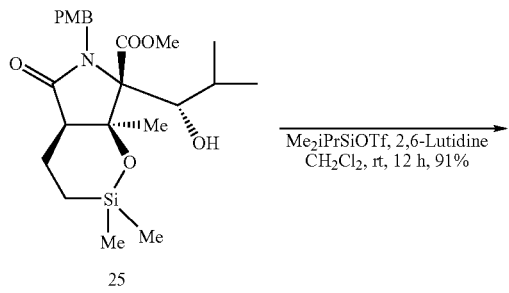

25

-continued

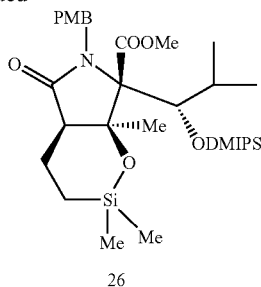

26

In Step 11, the free hydroxyl group in Compound 25 is protected by reation with dimethyl isopropyl silyltriflate and 2,6-lutidine.

Step 12:

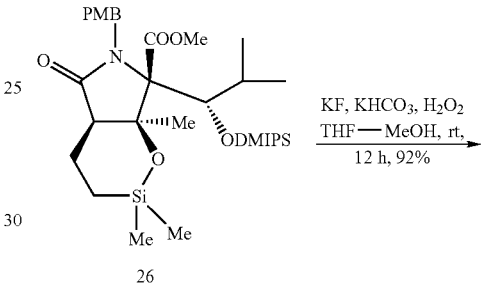

26

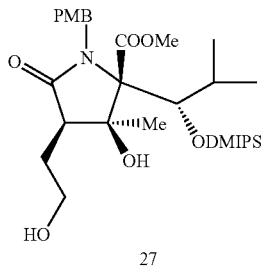

27

In Step 12, the bicyclic compound 26 is oxidized by treatment with hydrogen peroxide, potassium fluoride and potassium bicarbonate to yield Compound 27, without disturbing two protecting groups —PMB and dimethyl isopropyl silyl protecting group (DMIPS).

Step 13:

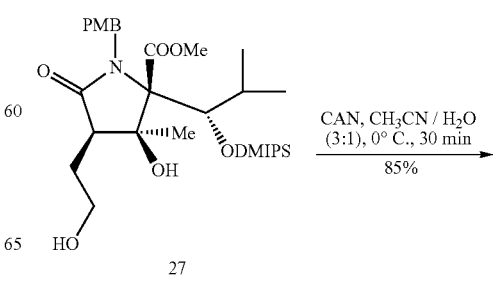

27

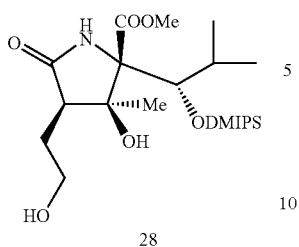

In Step 13, the amino protecting group PMB in Compound 27 is removed by reaction with ceric (IV) ammonium nitrate (CAN) affording Compound 28.

Step 14:

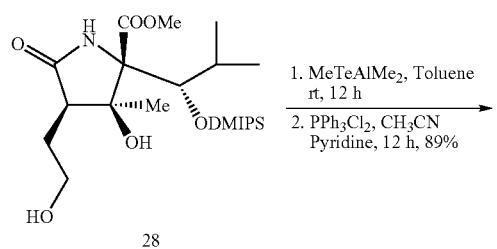

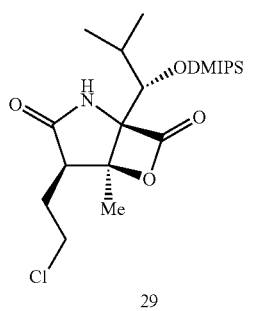

In Step 14, Compound 28 is converted, in a two-step procedure, to the beta-lactone of Compound 29—first by reaction with dimethylaluminum methyl tellurolate, followed by triphenylphosphine chloride.

Step 15:

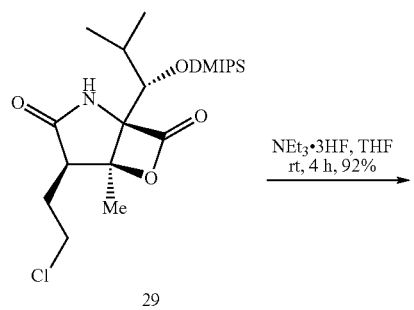

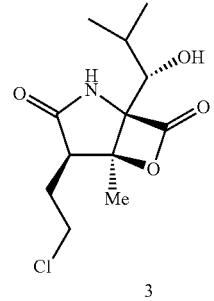

In Step 15, the DMIPS protecting group in Compound 29 is removed by treatment with triethylamine and hydrogen fluoride to afford Compound 3.

The preferred compounds of the present invention have the stereochemistry dictated by the natural product Salinosporamide A. However, additional embodiments of the present invention are directed to the following structural formulae, which are not limited to the stereochemistry of the natural products. The compounds of Formula I, II, and III, have the same substituent definitions used herein for the corresponding natural product analogs, namely the compounds of Formula Ia, Ia, and IIIa.

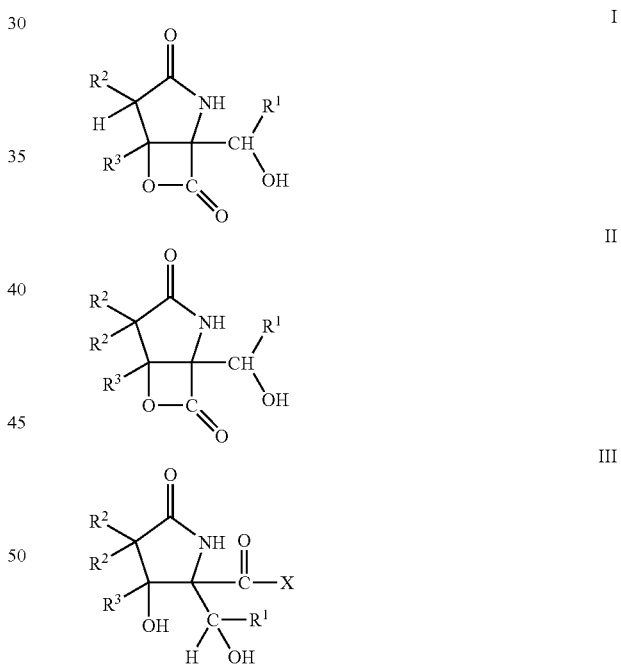

Utility of the Compounds of the Invention

The disclosed compounds may be used to treat conditions mediated directly by the proteolytic function of the proteasome such as muscle wasting, or mediated indirectly via proteins which are processed by the proteasome such as NF-kappaB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include beta-amyloid protein and regulatory proteins such as cyclins and transcription factor NF-kappaB. Treating as used herein includes reversing, reducing, or arresting the symptoms, clinical signs, and underlying pathology of a condition in manner to improve or stabilize the subject's condition.

Alzheimer's disease is characterized by extracellular deposits of beta-amyloid protein (beta-AP) in senile plaques and cerebral vessels. beta-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the beta-AP sequence, thereby preventing the generation of beta-AP. It is believed that abnormal protein processing by the proteasome contributes to the abundance of beta-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the beta-subunit of human macropain. Kojima, S. et al., Fed. Eur. Biochem. Soc., 1992, 304, 57-60. The APP-processing enzyme cleaves at the Gln15-Lys16 bond; in the presence of calcium ion, the enzyme also cleaves at the Met-1-Asp1 bond, and the Asp1-Ala2 bonds to release the extracellular domain of beta-AP.

One embodiment, therefore, is a method of treating Alzheimer's disease, including administering to a subject an effective amount of a compound (e.g., pharmaceutical composition) having a formula disclosed herein. Such treatment includes reducing the rate of beta-AP processing, reducing the rate of beta-AP plaque formation, and reducing the rate of beta-AP generation, and reducing the clinical signs of Alzheimer's disease.

Other embodiments of the invention relate to methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Proteasome inhibitors are useful for treating conditions such as cancer, chronic infectious diseases, fever, muscle disuse (atrophy) and denervation, nerve injury, fasting, renal failure associated with acidosis, and hepatic failure. See, e.g., U.S. Pat. No. 5,340,736. Additional embodiments of the invention therefore encompass methods of:

reducing the rate of muscle protein degradation in a cell,
reducing the rate of intracellular protein degradation,
reducing the rate of degradation of p53 protein in a cell, and
inhibiting the growth of p53 related cancers.

Each of these methods includes the step of contacting a cell (in vivo or in vitro, e.g., a muscle in a subject) with an effective amount of a compound (e.g., pharmaceutical composition) of a formula disclosed herein.

Another protein processed by the proteasome is NF-kappaB, a member of the Rel protein family. The Rel family of transcriptional activator proteins can be divided into two groups. The first group requires proteolytic processing, and includes p50 (NF-kappaB1, 105 kDa) and p52 (NF-kappa2, 100 kDa). The second group does not require proteolytic processing, and includes p65 (RelA, Rel (c-Rel), and RelB). Both homo- and heterodimers can be formed by Rel family members; NF-kappaB, for example, is a p50-p65 heterodimer. After phosphorylation and ubiquitination of IkappaB and p105, the two proteins are degraded and processed, respectively, to produce active NF-kappaB which translocates from the cytoplasm to the nucleus. Ubiquitinated p105 is also processed by purified proteasomes. Palombella et al., Cell 1994, 78, 773-785. Active NF-kappaB forms a stereospecific enhancer complex with other transcriptional activators and, e.g., HMG I(Y), inducing selective expression of a particular gene.

NF-kappaB regulates genes involved in the immune and inflammatory response, and mitotic events. For example, NF-kappaB is required for the expression of the immunoglobulin light chain kappa gene, the IL-2 receptor alpha-chain gene, the class I major histocompatibility complex gene, and a number of cytokine genes encoding, for example, IL-2, IL-6, granulocyte colony-stimulating factor, and IFN-beta. Palombella et al., supra. Some embodiments of the invention include methods of affecting the level of expression of IL-2, MHC-I, IL-6, IFN-beta or any of the other previously-mentioned proteins, each method including administering to a subject an effective amount of a compound of a formula disclosed herein.

NF-kappaB also participates in the expression of the cell adhesion genes that encode E-selectin, P-selectin, ICAm, and VCAM-1, Collins, T., Lab. Invest., 1993, 68, 499-508. One embodiment of the invention is a method of inhibiting cell adhesion (e.g., cell adhesion mediated by E-selectin, P-selectin, ICAm, or VCAM-1), including contacting a cell with (or administering to a subject) an effective amount of a compound (e.g., pharmaceutical composition) having a formula disclosed herein.

NF-kappaB also binds specifically to the HIV-enhancer/promoter. When compared to the Nef of mac239, the HIV regulatory protein Nef of pbj 14 differs by two amino acids in the region which controls protein kinase binding. It is believed that the protein kinase signals the phosphorylation of I-kappaB, triggering IkappaB degradation through the ubiquitin-proteasome pathway. After degradation, NF-kappaB is released into the nucleus, thus enhancing the transcription of HIV. Cohen, J., Science, 1995, 267, 960. Additional embodiments of the invention are a method of inhibiting or reducing HIV infection in a subject, and a method of decreasing the level of viral gene expression, each method including administering to the subject an effective amount of a compound of a formula disclosed herein.

Complexes including p50 are rapid mediators of acute inflammatory and immune responses. Thanos et al., Cell, 1995, 80, 529-532. Intracellular proteolysis generates small peptides for presentation to T-lymphocytes to induce MHC class I-mediated immune responses. The immune system screens for autologous cells that are virally infected or have undergone oncogenic transformation. Additional embodiments of the invention are a method of inhibiting antigen presentation in a cell, including exposing the cell to a compound of a formula described herein, and a method of suppressing the immune system of a subject (e.g., inhibiting transplant rejection), including administering to the subject an effective amount of a compound of a formula described herein.

In addition, the invention provides a method of treating inflammation, wherein the method includes administering to a subject an effective anti-inflammatory amount of a pharmaceutical composition containing a compound of a formula described herein. Inflammation can be a primary or secondary response associated with (a) injury such as a cut, laceration, puncture wound, (b) infection (including infected surgical incisions) by one or more viruses, bacteria, mycobacteria, microorganisms, parasites, and fungi, (c) allergies, (d) a disease state, (e) surgery (e.g., transplantation), or (f) a combination thereof.

Allergies are primary inflammatory responses to antigens or allergens. Sources of allergens include plants (e.g., grass or tree pollen), animals (e.g., dander, venom, urine, execreta from dogs, cats, insects, and snakes), and fungi. In addition to allergens such as rye grass, ragweed, and Japanese cedar pollen, certain foods or food components (e.g., eggs, milk, shellfish, strawberries, chocolate), vaccines, and drugs (e.g., penicillin) can induce allergic reactions in certain individuals.

Disease states include rheumatoid arthritis, scleroderma, rheumatic fever, inflammatory bowel disease (e.g., Crohn's disease and ulcerative colitis), diabetes mellitus, myasthenia gravis, multiple sclerosis, Guillain-Barre syndrome, conjunctiva of the eye, systemic lupus erythematosus, encephalitis, Adult Respiratory Distress Syndrome, psoriasis, emphysema, Alzheimer's disease, and muscular dystrophy.

The invention provides a method of treating inflammation induced by organ or tissue transplantation. This method includes administering to a patient who has undergone or is about to undergo transplantation a composition containing a compound having a formula disclosed herein. Transplantations include bone marrow, solid organ (e.g., kidney, lungs, heart, pancreas, liver, and skin), or tissues.

Certain proteasome inhibitors block both degradation and processing of ubquitinated NF-kappaB in vitro and in vivo. Proteasome inhibitors also block IkappaB-alpha degradation and NF-kappaB activation, Palombella et al.; and Traenckner et al., EMBO J., 1994, 13, 5433-5441. One embodiment of the invention is a method of inhibiting IkappaB-alpha degradation, including contacting the cell with a compound of a formula described herein. A further embodiment is a method of reducing the cellular content of NF-kappaB in a cell, muscle, organ, or subject, including contacting the cell, muscle, organ, or subject with a compound of a formula described herein.

Proteasome inhibitors are also useful for treatment of ischemic or reperfusion injury, particularly for preventing or reducing the size of infarct after vascular occlusion such as occurs during a stroke or heart attack, as described in U.S. Pat. No. 6,271,199. Proteasome inhibitors also block proteasome-dependent transformation of protozoan parasites (Gonzalez et al., J. Exp. Med., 1996, 84, 1909. Further embodiments of the invention therefore encompass methods for treating an infarct or a protozoan parasitic disease by administering a compound of a formula disclosed herein. In a preferred aspect of the invention, a compound of the present invention is administered to prevent or reduce the size of the infarct after vascular occlusion. Said compounds can be administered from about 0 to about 10 hours from the occurrence of a stroke in order to treat or reduce neuronal loss following an ischemic event.

Other eukaryotic transcription factors that require proteolytic processing include the general transcription factor TFIIA, herpes simplex virus VP 16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound of a formula disclosed herein. Cyclins are proteins involved in cell cycle control. The proteasome participates in the degradation of cyclins. Examples of cyclins include mitotic cyclins, G1 cyclins, (cyclin B). Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAALGN-ISEN-50 (destruction box). There is evidence that cyclin is converted to a form vulnerable to a ubiquitin ligase or that a cyclin-specific ligase is activated during mitosis. Ciechanover, A., Cell, 1994, 79, 13-21. Inhibition of the proteasome inhibits cyclin degradation, and therefore inhibits cell proliferation (e.g., cyclin-related cancers). Kumatori et al., Proc. Natl. Acad. Sci. USA, 1990, 87, 7071-7075. One embodiment of the invention is a method of treating a proliferative disease in a subject (e.g., cancer, psoriasis, or restenosis), including administering to the subject an effective amount of a compound of a formula disclosed herein. Chronic or acute inflammation can result from transplantation rejection, arthritis, rheumatoid arthritis, infection, dermatosis, inflammatory bowel disease, asthma, osteoporosis, and autoimmune diseases. Rejection or inflammation can occur in transplanted tissues or organs of any type, including heart, lung, kidney, liver, skin grafts, and tissue grafts. The invention also encompasses a method of treating cyclin-related inflammation in a subject, including administering to a subject an effective amount of a compound of a formula described herein.

Additional embodiments are methods for affecting the proteasome-dependent regulation of oncoproteins and methods of treating or inhibiting cancer growth, each method including exposing a cell (in vivo, e.g., in a subject or in vitro) to a compound of a formula disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method of treating p53-related apoptosis, including administering to a subject an effective amount of a compound of a formula disclosed herein.

Treatment of cancer prevents, alleviates, or ameliorates one or more primary or secondary phenomena associated with the initiation, progression, and metastasis of tumors, especially malignant tumors, e.g., a growth of tissue wherein cell multiplication is uncontrolled. Malignant tumors show a greater degree of anaplasia than do benign tumors. The invention provides a method of treating cancer including administering to a subject an effective anti-cancer amount of a pharmaceutical composition described herein, wherein the cancer is selected from carcinoma, lymphoma, sarcoma, and myeloma.

Examples of carcinomas include adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Examples of sarcomas include amelioblastic sarcoma, angiolithic sarcoma, botryoid sarcoma, endometrial stroma sarcoma, ewing sarcoma, fascicular sarcoma, giant cell sarcoma, granulocytic sarcoma, immunoblastic sarcoma, juxacordial osteogenic sarcoma, coppices sarcoma, leukocytic sarcoma (also known as leukemia), lymphatic sarcoma (also known as lympho sarcoma), medullary sarcoma, myeloid sarcoma (also known as granulocytic sarcoma), osteogenic sarcoma, periosteal sarcoma, reticulum cell sarcoma (also known as histiocytic lymphoma), round cell sarcoma, spindle cell sarcoma, synovial sarcoma, and telangiectatic audiogenic sarcoma. Examples of lymphomas include Hodgkin's disease and lymphocytic lymphomas, such as Burkitt's, nodular poorly-differentiated lymphocytic (NPDL), nodular mixed lymphocytic (NML), NH (nodular histiocytic), and diffuse lymphomas. Additional carcinomas include neural blastoma, glioblastoma, astrocytoma, melanoma, leiomyo sarcoma, multiple myeloma, and Hemangioma.

A tripeptide aldehyde protease inhibitor (benzyloxycarbonyl (Z)-Leu-Leu-leucinal induces neurite outgrowth in PC12 cells at an optimal concentration of 30 nM, Tsubuki et al., Biochem. and Biophys. Res. Comm., 1993, 196, 1195-1201. Peptide aldehydes have been shown to inhibit the chymotryptic activity of the proteasome. Vinitsky et al., 1992, Tsubuki et al., 1993. One embodiment of the invention is a method of promoting neurite outgrowth, including administering to the subject a compound of a formula disclosed herein.

Finally, the disclosed compounds are also useful as diagnostic agents (e.g., in diagnostic kits or for use in clinical laboratories) for screening for proteins (e.g., enzymes, transcription factors) processed by the proteasome. The disclosed compounds are also useful as research reagents for specifically binding the X/MB1 subunit or alpha-chain and inhibiting the proteolytic activities associated with it. For example, the activity of (and specific inhibitors of) other subunits of the proteasome can be determined.

Most cellular proteins are subject to proteolytic processing during maturation or activation. The compounds of the invention can be used to determine whether a cellular, developmental, or physiological process or output is regulated by the proteolytic activity of the proteasome. One such method includes obtaining an organism, an intact cell preparation, or a cell extract; exposing the organism, cell preparation, or cell extract to a compound of a formula disclosed herein; exposing the compound-exposed organism, cell preparation, or cell extract to a signal, and monitoring the process or output. The high selectivity of the compounds disclosed herein permits rapid and accurate elimination or implication of the proteasome in a given cellular, developmental, or physiological process.

Formulation and Administration

The methods of the invention contemplate treatment of animal subjects, such as mammals (e.g., higher primates, and especially humans). The invention encompasses pharmaceutical compositions which include novel compounds described herein, and pharmaceutical compositions which include compounds described and recognized herein as proteasome inhibitors.

Pharmaceutically acceptable salts may be formed, for example, with 1, 2, 3, or more equivalents of hydrogen chloride, hydrogen bromide, trifluoroacetic acid, and others known to those in the art of drug formulation. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-inflammatory, anti-cancer, or other agents. A subject may have more than one type of inflammation, or more than one type of cancer, a combination of allergies, or a mixture of the above conditions for which the disclosed compounds are useful. A compound of the invention may be administered in unit dosage form, and may be prepared by any of the methods well known in the pharmaceutical art, for example, as described in Remington's Pharmaceutical Sciences (Mack Pub. Co., Easton, Pa., 1980). The invention also encompasses a packaged drug, containing a pharmaceutical composition formulated into individual dosages and printed instructions for self-administration.

Compounds disclosed herein as proteasome inhibitors may be prepared for use in parenteral administration in the form of solutions or liquid suspensions; for oral administration (preferable), particularly in the form of tablets or capsules; or intranasally, particularly in the form of powders, gels, oily solutions, nasal drops, aerosols, or mists. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene. Additional parental delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 0.1-10% w/v of compound for parenteral administration. Typical dose ranges are from about 0.1 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

The effective amount of the active compound used to practice the present invention for treatment of conditions directly or indirectly mediated by the proteasome varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount."

Experimental Details of Scheme 1

General

All moisture sensitive reactions were performed under nitrogen gas in glassware that was flame-dried and equipped with a magnetic stir bar. Tetrahydrofuran (THF) and 1,2-dimethoxyethane (DME) were freshly distilled from sodium benzophenone ketyl before use. Hexanes, pyridine, triethylamine, pentane and dichloromethane were freshly distilled from $CaH_2$ before use. Toluene was distilled from sodium.

Thin-layer chromatography (TLC) was performed using E. Merck silica gel 60 $F_{254}$ pre-coated plates (0.25 mm). Flash chromatography was performed using Baker silica gel (40 μm particle size). All products were purified to homogeneity by TLC analysis (single spot/two solvent systems) using a UV lamp or CAM or PMA or anisaldehyde or basic $KMnO_4$ for detection purposes.

NMR spectra were recorded on 400 MHz, 500 MHz and 600 MHz spectrometers. $^1$H and $^{13}$C NMR chemical shifts are reported as δ using residual solvent as an internal standard. High-resolution mass spectral analyses were performed at Harvard University Mass Spectrometry Center.

EXAMPLE 1

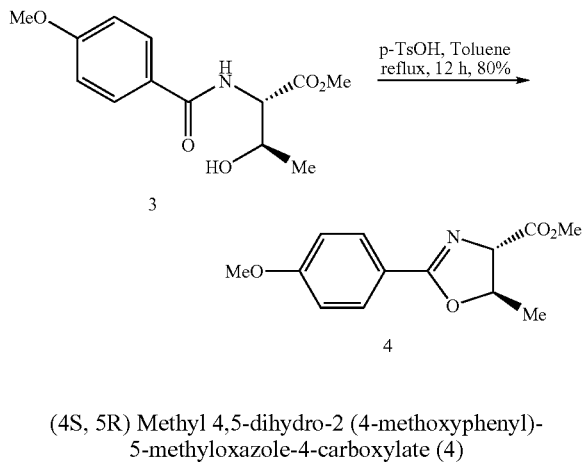

(4S, 5R) Methyl 4,5-dihydro-2 (4-methoxyphenyl)-5-methyloxazole-4-carboxylate (4)

A mixture of (2S, 3R)-methyl 2-(4-methoxybenzamido)-3-hydroxybutanoate (3) (35.0 g, 131 mmol) and p-TsOH.H$_2$O (2.5 g, 13.1 mmol) in toluene (400 mL) was heated at reflux for 12 h. The reaction mixture was diluted with water (200 mL) and extracted with EtOAc (3×200 mL). The combined organic layers were washed with water, brine and dried over Na$_2$SO$_4$. The solvent was removed in vacuo to give crude oxazoline as yellow oil. Flash column chromatography on silica gel (eluent 15% EtOAc-Hexanes) afforded the pure oxazoline (26.1 g, 80%) as solid.

$R_f$=0.51 (50% ethyl acetate in hexanes), mp. 86-87° C.; $[\alpha]^{23}_D$ +69.4 (c 2.0, CHCl$_3$); FTIR (film) $v_{max}$: 2955, 1750, 1545, 1355, 1187, 1011, 810 cm$^{-1}$; $^1$H NMR(CDCl$_3$, 400 MHz): δ 7.87 (2H, d, J=9.2 Hz), 6.84 (2H, d, J=8.8 Hz), 4.90 (1H, m), 4.40 (1H, d, J=7.6 Hz), 3.79 (3H, s), 3.71 (3H, s), 1.49 (3H, d, J=6.0 Hz); $^{13}$C NMR (CDCl$_3$, 100 MHz): δ 171.93, 165.54, 162.64, 130.52, 119.80, 113.85, 78.91, 75.16, 55.51, 52.73, 21.14; HRMS (ESI) calcd for C$_{13}$H$_{16}$NO$_4$ (M+H)$^+$.250.1079, found 250.1084.

EXAMPLE 2

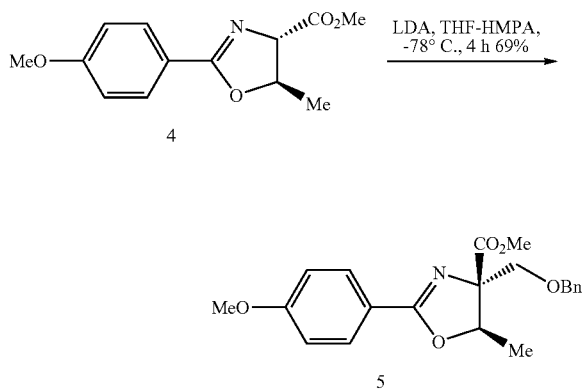

(4R, 5R)-Methyl 4-{(benzyloxy) methyl)}-4,5-dihydro-2-(4-methoxyphenyl)-5-methyloxazole-4-carboxylate (5)

To a solution of LDA (50 mmol, 1.0 M stock solution in THF) was added HMPA (24 mL, 215 mmol) at −78° C. and then oxazoline 4 (12.45 g, 50 mmol, in 20 mL THF) was added dropwise with stirring at −78° C. for 1 h to allow complete enolate formation. Benzyloxy chloromethyl ether (8.35 mL, 60 mmol) was added at this temperature and after stirring the mixture at −78° C. for 4 h, it was quenched with water (50 mL) and warmed to 23° C. for 30 min. Then the mixture was extracted with ethyl acetate (3×50 mL) and the combined organic phases were dried (MgSO$_4$) and concentrated in vacuo. The crude product was purified by column chromatography (silica gel, ethyl acetate/hexanes, 1:4 then 1:3) to give the benzyl ether 5 (12.7 g, 69%).

$R_f$=0.59 (50% ethyl acetate in hexanes). $[\alpha]^{23}_D$ −6.3 (c 1.0, CHCl$_3$); FTIR (film) ($v_{max}$: 3050, 2975, 1724, 1642, 1607, 1252, 1027, 745, 697 cm$^{-1}$; $^1$H NMR (CDCl$_3$, 400 MHz): δ 7.96 (2H, d, J=9.2 Hz), 7.26 (5H, m), 6.90 (2H, J=8.8 Hz), 4.80 (1H, m), 4.61 (2H, s), 3.87 (3H, m), 3.81 (3H, s), 3.73 (3H, s), 1.34 (3H, d, J=6.8 Hz); $^{13}$C NMR (CDCl$_3$, 100 MHz): δ 171.23, 165.47, 162.63, 138.25, 130.64, 128.52, 127.87, 127.77, 120.15, 113.87, 81.40, 79.92, 73.91, 73.43, 55.58, 52.45, 16.92; HRMS (ESI) calcd for C$_{21}$H$_{24}$O$_5$ (M+H)$^+$ 370.1654, found 370.1644.

EXAMPLE 3

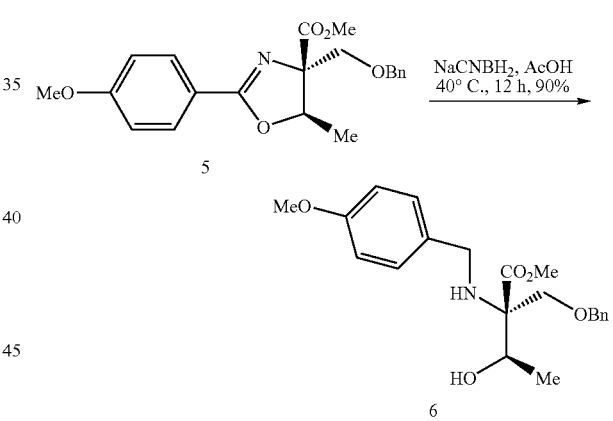

(2R,3R)-Methyl 2-(4-methoxybenzylamino)-2-((benzyloxy)methyl)-3hydroxybutanoate (6)

To a solution of oxazoline 5 (18.45 g, 50 mmol) in AcOH (25 mL) at 23° C. was added in portions NaCNBH$_3$ (9.3 g, 150 mmol). The reaction mixture was then stirred at 40° C. for 12 h to allow complete consumption of the starting material. The reaction mixture was diluted with water (100 mL), neutralized with solid Na$_2$CO$_3$ and the aqueous layer was extracted with ethyl acetate (3×100 mL). The combined organic phases were dried over NaSO$_4$ and concentrated in vacuo. The crude product was purified by column chromatography (silica gel, ethyl acetate/hexanes, 1:5) to give the N-PMB amino alcohol 6 (16.78 g, 90%).

$R_f$=0.50 (50% ethyl acetate in hexanes). $[\alpha]^{23}_D$ −9.1(c 1.0, CHCl$_3$); FTIR (film) $v_{max}$: 3354, 2949, 1731, 1511, 1242, 1070, 1030, 820, 736, 697 cm$^{-1}$; $^1$H NMR (CDCl$_3$, 400

MHz): δ 7.32 (7H, m), 6.87 (2H, d, J=8.8 Hz), 4.55 (2H, m), 4.10 (1H, q, J=6.4 Hz), 3.85 (2H, dd, J=17.2, 10.0 Hz), 3.81 (3H, s,), 3.77 (3H, s), 3.69 (2H, dd, J=22.8, 11.6 Hz), 3.22 (2H, bs), 1.16 (3H, d, J=6.0 Hz); $^{13}$C NMR (CDCl$_3$, 100 MHz): δ 173.34, 159.03, 137.92, 132.51, 129.78, 128.67, 128.07, 127.98, 114.07, 73.80, 70.55, 69.82, 69.65, 55.51, 55.29, 47.68, 18.15; HRMS (ESI) calcd. for $C_{21}H_{28}NO_5$ (M+H)$^+$ 374.1967, found 374.1974.

EXAMPLE 4

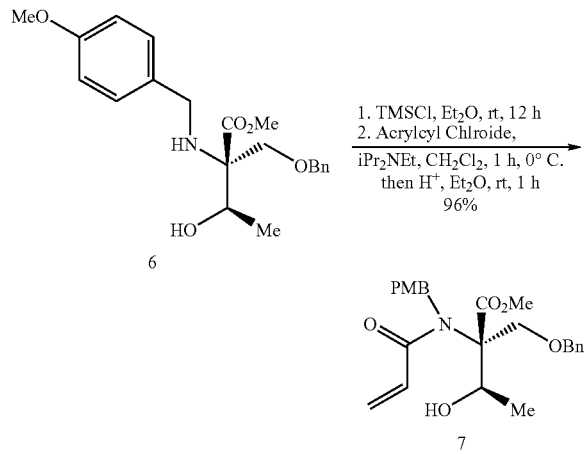

(2R,3R)-Methyl-2-(N-(4-methoxybenzyl)acrylamido)-2-(benzyloxy)methyl)-3-hydroxybutanoate (7)

A solution of amino alcohol 6 (26.2 g, 68.5 mmol) in Et$_2$O (200 mL) was treated with Et$_3$N (14.2 mL, 102.8 mmol) and trimethylchlorosilane (10.4 mL, 82.2 mmol) at 23° C. and stirred for 12 h. After completion, the reaction mixture was diluted with ether (200 mL) and then resulting suspension was filtered through celite. The solvent was removed to furnish the crude product (31.2 g, 99%) in quantitative yield as viscous oil. A solution of this crude trimethylsilyl ether (31.1 g) in CH$_2$Cl$_2$ (200 mL) was charged with diisopropylethylamine (14.2 mL, 81.6 mmol) and then cooled to 0° C. Acryloyl chloride (6.64 mL, 82.2 mmol) was added dropwise with vigorous stirring and the reaction temperature was maintained at 0° C. until completion (1 h). The reaction mixture was then diluted with CH$_2$Cl$_2$ (100 mL) and the organic layer was washed with water and brine. The organic layer was separated and dried over Na$_2$SO$_4$. The solvent was removed to afford the crude acrylamide 7 as a viscous oil. The crude product was then dissolved in Et$_2$O (200 mL) and stirred with 6N HCl (40 mL) at 23° C. for 1 h. The reaction mixture was diluted with water (100 mL) and concentrated to provide crude product. The residue was purified by column chromatography (silica gel, ethyl acetate/hexanes, 1:5 to 1:1) to give pure amide 7 (28.3 g, 96%) as colorless solid, mp 88-89° C.

R$_f$=0.40 (50% ethyl acetate in hexanes), $[\alpha]^{23}_D$ −31.1 (c 0.45, CHCl$_3$), FTIR (film) v$_{max}$: 3435, 2990, 1725, 1649, 1610, 1512, 1415, 1287, 1242, 1175, 1087, 1029, 732, 698 cm$^{-1}$; $^1$H NMR (CDCl$_3$, 500 MHz): δ 7.25 (5H, m), 7.15 (2H, d, J=6.5 Hz), 6.85 (2H, d, J=7.5 Hz), 6.38 (2H, d, J=6.0 Hz), 5.55 (1H, t, J=6.0 Hz), 4.81 (2H, s), 4.71 (1H, q, J=6.5 Hz), 4.35 (2H, s), 4.00 (1H, d, J=10.0 Hz), 3.80 (1H, d, J=10.0 Hz), 3.76 (3H, s), 3.75 (3H, s), 3.28 (1H, bs), 1.22 (3H, d, J=6.0 Hz); $^{13}$C NMR (CDCl$_3$, 125 MHz): δ 171.87, 168.74, 158.81, 137.73, 131.04, 129.68, 128.58, 128.51, 127.94, 127.72, 127.20, 127.14, 114.21, 73.71, 70.42, 69.76, 67.65, 55.45, 52.52, 49.09, 18.88; HRMS (ESI) calcd. for $C_{24}H_{30}NO_6$ (M+H)$^+$428.2073, found 428.2073.

EXAMPLE 5

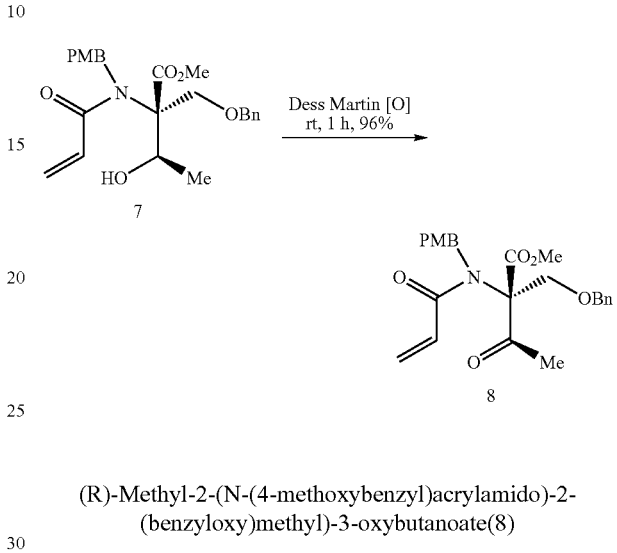

(R)-Methyl-2-(N-(4-methoxybenzyl)acrylamido)-2-(benzyloxy)methyl)-3-oxybutanoate(8)

To a solution of amide 7 (10.67 g, 25.0 mmol) in CH$_2$Cl$_2$ (100 mL) was added Dess-Martin periodinane reagent (12.75 g, 30.0 mmol, Aldrich Co.) at 23° C. After stirring for 1 h, the reaction mixture was quenched with aq NaHCO$_3$—Na$_2$S$_2$O$_3$ (1:1, 50 mL) and extracted with ethyl acetate (3×50 mL). The organic phase was dried and concentrated in vacuo to afford the crude ketone. The crude product was purified by column chromatography (silica gel, ethyl acetate/hexanes) to give pure keto amide 8 (10.2 g, 96%).

R$_f$=0.80 (50% ethyl acetate in hexanes), mp 85 to 86° C.; $[\alpha]^{23}_D$ −12.8 (c 1.45, CHCl$_3$); FTIR(film) v$_{max}$:3030, 2995, 1733, 1717, 1510, 1256, 1178, 1088, 1027, 733, 697 cm$^{-1}$; $^1$H NMR (CDCl$_3$, 500 MHz): δ 7.30 (2H, d, J=8.0), 7.25 (3H, m), 7.11 (2H, m), 6.88 (2H, d, J=9.0 Hz), 6.38 (2H, m), 5.63 (1H, dd, J=8.5, 3.5 Hz), 4.93 (1H, d, J=18.5 Hz), 4.78 (1H, d, J=18.5, Hz), 4.27 (2H, m), 3.78 (3H, s), 3.76 (3H, s), 2.42 (3H, s); $^{13}$C NMR(CDCl$_3$, 125 MHz): δ 198.12, 169.23, 168.62, 158.01, 136.95, 130.64, 130.38, 128.63, 128.13, 127.77, 127.32, 114.33, 77.49, 73.97, 70.66, 55.49, 53.09, 49.03, 28.24; HRMS (ESI) calcd. for $C_{24}H_{28}NO_6$ (M+H)$^+$ 426.1916, found 426.1909.

EXAMPLE 6

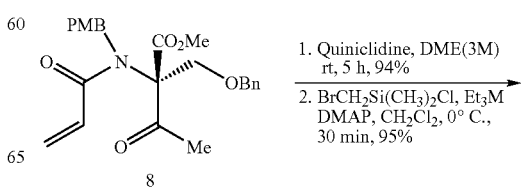

-continued

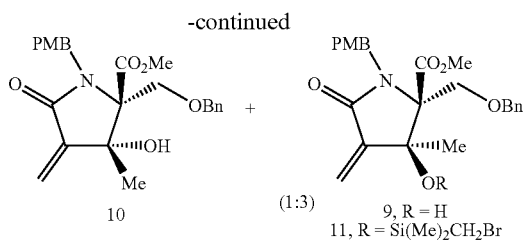

(2R,3S)-Methyl-1-(4-methoxybenzyl)-2-((benzyloxy)methyl)-3-hydroxy-3-methyl-4-methylene-5-oxopyrrolidine-2-carboxylate (9+10)

A mixture of keto amide 8 (8.5 g, 20.0 mmol) and quinuclidine (2.22 g, 20.0 mmol) in DME (10 mL) was stirred for 5 h at 23° C. After completion, the reaction mixture was diluted with ethyl acetate (50 mL) washed with 2N HCl, followed by water and dried over $Na_2SO_4$. The solvent was removed in vacuo to give the crude adduct (8.03 g, 94.5%, 3:1 ratio of 9 to 10 dr) as a viscous oil. The diastereomeric mixture was separated at the next step, although small amounts of 9 and 10 were purified by column chromatography (silica gel, ethyl acetate/hexanes, 1:10 to 1:2) for analytical purposes.

Major Diastereomer (9).

$[α]^{23}_D$ −37.8 (c 0.51, $CHCl_3$); FTIR (film) $v_{max}$: 3450, 3055, 2990, 1733, 1683, 1507, 1107, 1028, 808, 734 cm$^{-1}$; $^1H$ NMR ($CDCl_3$, 500 MHz): δ 7.29 (5H, m), 7.15 (2H, d, J=7.5 Hz), 6.74 (2H, d, J=8.5 Hz), 6.13 (1H, s), 5.57 (1H,s), 4.81 (1H, d, J=14.5 Hz), 4.45(1H, d, J=15.0 Hz), 4.20 (1H, d, J=12.0 Hz), 4.10 (1H, d, J=12.0 Hz) 3.75 (3H, s), 3.70 (1H, d, J=10.5 Hz), 3.64 (3H, s), 3.54 (1H, d, J=10.5 Hz), 2.55 (1H, bs, OH), 1.50 (3H, s); $^{13}C$ NMR ($CDCl_3$, 125 MHz): δ 169.67, 168.42, 158.97, 145.96, 137.57, 130.19, 130.12, 128.53, 127.83, 127.44, 116.79, 113.71, 76.32, 76.00, 73.16, 68.29, 55.45, 52.63, 45.36, 22.64; HRMS (ESI) calcd. for $C_{24}H_{28}NO_6$ (M+H)$^+$ 426.1916, found 426.1915.

Minor Diastereomer (10).

$[α]^{23}_D$ −50.1 (c 0.40, $CHCl_3$); FTIR (film) $v_{max}$: 3450, 3055, 2990, 1733, 1683, 1507, 1107, 1028, 808, 734 cm$^{-1}$; $^1H$ NMR ($CDCl_3$, 500 MHz): δ 7.29 (5H, m), 7.12 (2H, d, J=7.5 Hz), 6.73 (2H, d, J=8.5 Hz), 6.12 (1H, s), 5.57 (1H, s), 4.88 (1H, d, J=15.5 Hz), 4.31 (1H, d, J=15.0 Hz), 4.08 (3H, m), 3.99 (1H, d, J=12.0 Hz) 3.73 (3H, s), 3.62 (3H, s), 3.47 (1H, bs, OH), 3.43 (1H, d, J=10.0 Hz), 1.31 (3H, s); $^{13}C$ NMR ($CDCl_3$, 125 MHz): δ 169.65, 167.89, 159.13, 147.19, 136.95, 130.29, 129.76, 128.74, 128.19, 127.55, 116.80, 113.82, 76.21, 75.66, 73.27, 68.02, 55.45, 52.52, 45.24, 25.25; HRMS (ESI) calcd. for (M+H)$^{+C}_{24}H_{28}NO_6$ 426.1916, found 426.1915.

EXAMPLE 7

Silylation of 9 and 10 and Purification of 11.

To a solution of lactams 9 and 10 (7.67 g, 18 mmol) in $CH_2Cl_2$ (25 ml) was added $Et_3N$ (7.54 ml, 54 mmol), and DMAP (2.2 g, 18 mmol) at 0° C., and then bromomethyldimethylchlorosilane (5.05 g, 27 mmol) (added dropwise). After stirring the mixture for 30 min at 0° C., it was quenched with aq $NaHCO_3$ and the resulting mixture was extracted with ethyl acetate (3×50 mL). The combined organic layers were washed with water, brine and dried over $Na_2SO_4$. The solvent was removed in vacuo to give a mixture of the silated derivatives of 9 and 10 (9.83 g, 95%). The diastereomers were purified by column chromatography (silica gel, ethyl acetate/hexanes, 1:5 to 1:4) to give pure diastereomer 11 (7.4 g, 72%) and its diastereomer (2.4 g, 22%).

Silyl Ether (11).

$R_f$ =0.80 (30% ethyl acetate in hexanes). $[α]^{23}_D$ −58.9 (c 0.55, $CHCl_3$); FTIR (film) $v_{max}$: 3050, 2995, 1738, 1697, 1512, 1405, 1243, 1108, 1003, 809, 732 cm$^{-1}$; $^1H$ NMR ($CDCl_3$, 500 MHz): δ 7.27 (5H, m), 7.05 (2H, d, J=7.0 Hz), 6.71 (2H, d, J=8.5 Hz), 6.18 (1H, s), 5.53 (1H,s), 4.95 (1H, d, J=15.5 Hz), 4.45 (1H, d, J=15.0 Hz), 4.02 (1H, J=12.0 Hz), 3.86 (1H, d, J=11.5 Hz) 3.72 (3H, s), 3.68 (3H, s), 3.65 (1H, d, J=10.5 Hz), 3.30 (1H, d, J=10.0 Hz), 2.34 (2H, d, J=2.0 Hz), 1.58 (3H, s), 0.19 (3H, s), 0.18 (3H, s); $^{13}C$ NMR ($CDCl_3$, 125 MHz): δ 168.62, 168.12, 158.93, 145.24, 137.53, 130.32, 130.30, 128.49, 127.76, 127.22, 117.26, 113.60, 78.55, 78.03, 72.89, 68.45, 55.43, 52.37, 45.74, 21.87, 17.32, −0.72, −0.80; HRMS (ESI) Calcd. for $C_{27}H_{35}BrNO_6Si$ (M+H)$^+$ 576.1417, found 576.1407.

EXAMPLE 8

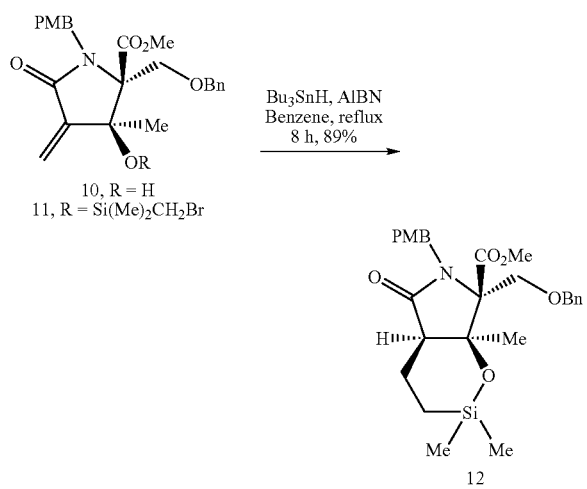

Conversion of (11) to (12).

To a solution of compound 11 (5.67 g 10 mmol) in benzene (250 mL) at 80° C. under nitrogen was added a mixture of tributyltin hydride (4.03 ml, 15 mmol) and AIBN (164 mg, 1 mmol) in 50 ml benzene by syringe pump over 4 h. After the addition was complete, the reaction mixture was stirred for an additional 4 h at 80° C. and the solvent was removed in vacuo. The residue was dissolved in hexanes (20 mL) and washed with saturated $NaHCO_3$ (3×25 mL), water and dried over $Na_2SO_4$. The solvent was removed in vacuo to give crude product. The crude product was purified by column chromatography (silica gel, ethyl acetate/hexanes, 1:5) to afford the pure 12 (4.42 g, 89%).

$R_f$=0.80 (30% ethyl acetate in hexanes). $[α]^{23}_D$ −38.8 (c 0.25, $CHCl_3$); FTIR (film) $v_{max}$: 3025, 2985, 1756, 1692, 1513, 1247, 1177, 1059, 667 cm$^{-1}$; $^1H$ NMR ($CDCl_3$, 500 MHz): δ 7.28 (5H, m), 7.09 (2H, d, J=7.0 Hz), 6.73 (2H, d, J=9.0 Hz), 4.96(1H, d, J=15.0 Hz), 4.35 (1H,d, J=15.5 Hz), 3.97 (1H, d, J=12.5 Hz), 3.86 (1H, d, J=12.0 Hz), 3.80 (1H, d, J=10.0 Hz), 3.72 (3H, s), 3.65 (3H, s), 3.27 (1H, d, J=10.5 Hz), 2.67 (1H, t, J=4.0 Hz), 2.41 (1H, m), 1.79 (1H, m), 1.46

(3H, s), 0.77 (1H, m), 0.46 (1H, m), 0.10 (3H, s), 0.19 (3H, s); $^{13}$C NMR (CDCl$_3$, 125 MHz): δ 175.48, 169.46, 158.76, 137.59, 131.04, 129.90, 128.58, 127.88, 127.52, 113.59, 113.60, 81.05, 78.88, 73.12, 69.03, 55.45, 51.94, 48.81, 45.50, 22.79, 17.06, 7.76, 0.54; HRMS (ESI) calcd. for (M+H)$^+$C$_{27}$H$_{36}$NO$_6$Si 498.2312, found 498.2309.

EXAMPLE 9

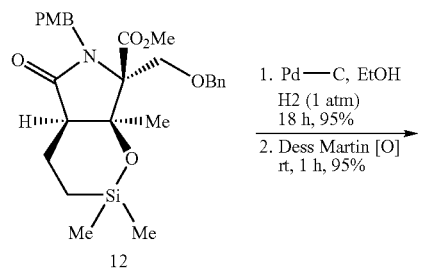

Debenzylation of (12).

A solution of 12 (3.98 g, 8 mmol) in EtOH (50 ml) at 23° C. was treated with 10% Pd—C (~1 g) under an argon atmosphere. The reaction mixture was evacuated and flushed with H$_2$ gas (four times) and then stirred vigorously under an atmosphere of H$_2$ (1 atm, H$_2$ balloon) at 23° C. After 12 h, the reaction mixture was filtered through Celite and concentrated in vacuo to give the crude debenzylation product (3.08 g, 95%) which was used for the next step. A small amount crude product was purified by column chromatography (silica gel, ethyl acetate/hexanes, 1:3) for analytical purposes. R$_f$=0.41 (50% ethyl acetate in hexanes).

mp, 45-47° C.; [α]$^{23}_D$ –30.9 (c 0.55, CHCl$_3$); FTIR (film) v$_{max}$: 3432, 3020, 2926, 1735, 1692, 1512, 1244, 1174, 1094, 1024, 870, 795 cm$^{-1}$; $^1$H NMR (CDCl$_3$, 400 MHz): δ 7.36 (2H, d, J=8.5 Hz), 6.83 (2H, d, J=8.5 Hz), 5.16 (1H, d, J=15.0 Hz), 4.29 (1H, d, J=15.0 Hz), 3.92 (1H, m), 3.78 (3H, s), 3.68 (3H, s), 3.45 (1H, m), 2.53 (1H, t, J=4.0 Hz), 2.42 (1H, m), 1.82 (1H, m), 1.50 (3H, s), 1.28 (1H, m), 0.75 (1H, m), 0.47 (1H, m), 0.11 (3H, s), 0.02 (3H, s); $^{13}$C NMR(CDCl$_3$, 125 MHz): δ 175.82, 169.51, 159.32, 131.00, 129.72, 114.52, 80.79, 80.13, 61.85, 55.48, 51.99, 49.29, 45.06, 23.11, 17.03, 7.44, 0.54; HRMS (ESI) calcd. for C$_{20}$H$_{30}$NO$_6$Si (M+H)$^+$ 408.1842, found 408.1846.

EXAMPLE 10

Oxidation to Form Aldehyde (13).

To a solution of the above alcohol from debenzylation of 12 (2.84 g, 7 mmol) in CH$_2$Cl$_2$ (30 mL) was added Dess-Martin reagent (3.57 g, 8.4 mmol) at 23° C. After stirring for 1 h at 23° C., the reaction mixture was quenched with aq NaHCO$_3$—Na$_2$S$_2$O$_3$ (1:1, 50 mL) and extracted with ethyl acetate (3×50 mL). The organic phase was dried and concentrated in vacuo to afford the crude aldehyde. The crude product was purified by column chromatography (silica gel, ethyl acetate/hexanes, 1:5) to give pure aldehyde 13 (2.68 g, 95%). R$_f$=0.56 (50% ethyl acetate in hexanes).

mp, 54-56° C.; [α]$^{23}_D$ –16.5 (c 0.60, CHCl$_3$); FTIR (film) v$_{max}$: 3015, 2925, 1724, 1702, 1297, 1247, 1170, 1096, 987, 794 cm$^{-1}$; $^1$H NMR (CDCl$_3$, 500 MHz): δ 9.62 (1H, s), 7.07 (2H, d, J=8.0 Hz), 6.73 (2H, d, J=8.5 Hz), 4.49 (1H, quart, J=8.5 Hz), 3.70 (3H, s), 3.67 (3H, s), 2.36 (2H, m), 1.75 (1H, m), 1.37 (3H, s), 0.73 (1H, m), 0.48 (1H, m), 0.07 (3H, s), 0.004 (3H, s); $^{13}$C NMR (CDCl$_3$, 125 MHz): δ 197.26, 174.70, 167.36, 158.07, 130.49, 128.96, 113.81, 83.97, 82.36, 55.34, 52.43, 47.74, 46.32, 23.83, 16.90, 7.52, 0.56, 0.45; HRMS (ESI) calcd. for C$_{20}$H$_{28}$NO$_6$Si (M+H)$^+$ 406.1686, found 406.1692.

EXAMPLE 11

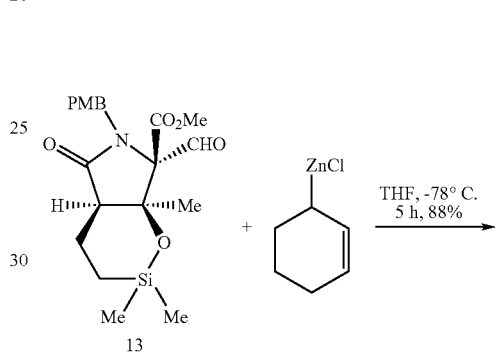

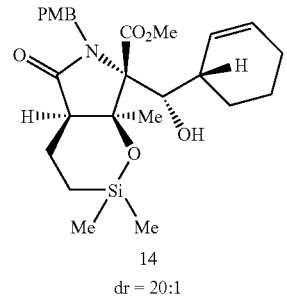

Conversion of (13) to (14).

To a solution of freshly prepared cyclohexenyl zinc chloride (10 mL, 0.5 M solution in THF, 5 mmol) (see Example 15 below) at –78° C. under nitrogen was added a –78° C. solution of aldehyde 13 (1.01 g, in 3 ml of THF, 2.5 mmol). After stirring for 5 h at –78° C. reaction mixture was quenched with water (10 mL) then extracted with ethyl acetate (3×10 mL). The combined organic layers were dried over Na$_2$SO$_4$ and solvent was removed in vacuo to give crude product (20:1 dr). The diastereomers were purified by column chromatography (silica gel, ethyl acetate/hexanes, 1:10 to 1:2 affords the pure major diastereomer 14 (1.0 g, 83%) and a minor diastereomer (50 mg 5%). For 14: R$_f$=0.56 (50% ethyl acetate in hexanes).

mp, 79-81° C.; [α]$^{23}_D$ –28.5 (c 1.45, CHCl$_3$); FTIR (film) v$_{max}$: 3267, 2927, 2894, 2829, 1742, 1667, 1509, 1248, 1164, 1024, 795 cm$^{-1}$; $^1$H NMR (CDCl$_3$, 500 MHz): δ 7.34 (2H, d, J=8.5 Hz), 6.81 (2H, d, J=9.0 Hz), 5.84 (1H, m), 5.73 (1H, m), 4.88 (1H, d, J=15.5 Hz), 4.39 (1H, d, J=14.5 Hz), 4.11 (1H, t, J=6.5 Hz), 3.77 (3H, s), 3.58 (3H, s), 3.00 (1H, m), 2.95 (1H, d, J=9.0 Hz), 2.83 (1H, t, J=3.5 Hz), 3.36 (1H, m), 2.27 (1H, m), 1.98 (2H, m), 1.74 (3H, m), 1.62 (3H, s), 1.14 (2H, m), 0.59 (1H, m), 0.39 (11H, m), 0.13 (3H, s), 0.03 (3H, s); $^{13}$C NMR (CDCl$_3$, 125 MHz): δ 176.80, 170.03, 158.27, 131.86, 131.34, 128.50, 126.15, 113.40, 83.96, 82.45, 77.17, 55.45, 51.46, 48.34, 48.29, 39.08, 28.34, 25.29, 22.45, 21.09, 17.30, 7.75, 0.39, 0.28; HRMS (ESI) calcd. for C$_{26}$H$_{38}$NO$_6$Si (M+H)$^+$ 488.2468, found 488.2477.

EXAMPLE 12

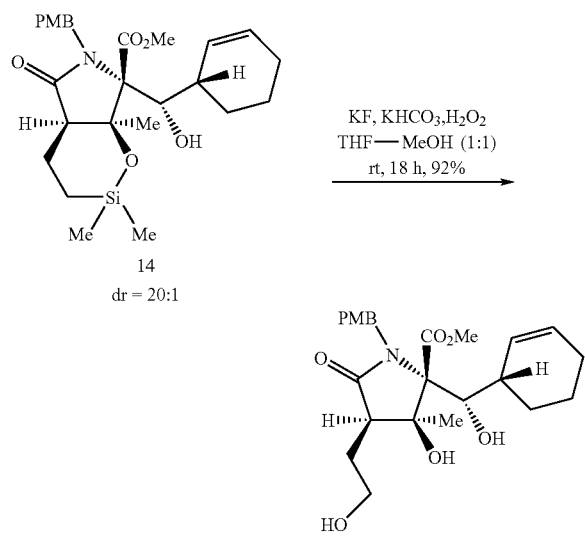

Tamao-Fleming Oxidation of (14) to (15).

To a solution of 14 (0.974 g, 2 mmol) in THF (5 mL) and MeOH (5 mL) at 23° C. was added KHCO$_3$ (0.8 g, 8 mmol) and KF (0.348 g, 6 mmol). Hydrogen peroxide (30% in water, 5 mL) was then introduced to this mixture. The reaction mixture was vigorously stirred at 23° C. and additional hydrogen peroxide (2 ml) was added after 12 h. After 18h, the reaction mixture was quenched carefully with NaHSO$_3$ solution (15 mL). The mixture was extracted with ethyl acetate (3×25 mL) and the combined organic layers were washed with water and dried over Na$_2$SO$_4$. The solvent was removed in vacuo to give the crude product. The crude product was purified by column chromatography (silica gel, ethyl acetate) to give the pure triol 15 (0.82 g, 92%).

R$_f$=0.15 (in ethyl acetate). mp, 83-84° C.; [α]$^{23}$$_D$: +5.2 (c 0.60, CHCl$_3$); FTIR (film) ν$_{max}$: 3317, 2920, 2827, 1741, 1654, 1502, 1246, 1170, 1018, 802 cm$^{-1}$; $^1$H NMR (CDCl$_3$, 500 MHz): δ 7.77 (2H, d, J=8.0 Hz), 6.28 (2H, d, J=8.0 Hz), 5.76 (1H, m), 5.63 (1H, d, J=10.0 Hz), 4.74 (1H, d, J=15.5 Hz), 4.54 (1H, d, J=15.0 Hz), 4.12 (1H, d, J=2.5 Hz), 3.80 (1H, m), 3.76 (3H, s), 3.72 (1H, m), 3.68 (3H, s), 3.00 (1H, m), 2.60 (1H, br), 2.20 (1H, m), 1.98 (2H, s), 1.87 (1H, m), 1.80 (1H, m), 1.71 (2H, m), 1.61 (3H, s), 1.14 (2H, m); $^{13}$C NMR (CDCl$_3$, 125 MHz): δ 178.99, 170.12, 158.27, 131.30, 130.55, 128.13, 126.39, 113.74, 81.93, 80.75, 76.87, 61.61, 55.45, 51.97, 51.32, 48.07, 39.17, 27.71, 27.13, 25.22, 21.35, 21.22; HRMS (ESI) calcd. for C$_{24}$H$_{34}$NO$_7$ (M+H)$^+$ 448.2335, found 448.2334.

EXAMPLE 13

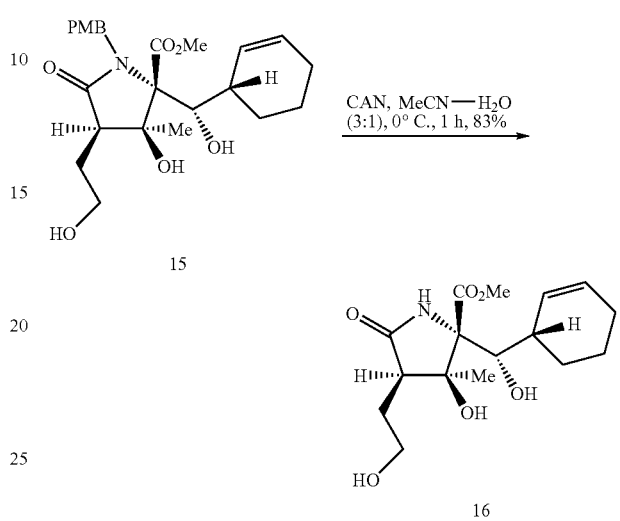

Deprotection of (15) to (16).

To a solution of 15 (0.670 g, 1.5 mmol) in acetonitrile (8 mL) at 0° C. was added a pre-cooled solution of ceric ammonium nitrate (CAN) (2.46 g 4.5 mmol in 2 mL H$_2$O). After stirring for 1 h at 0° C. the reaction mixture was diluted with ethyl acetate (50 mL), washed with saturated NaCl solution (5 mL) and organic layers was dried over Na$_2$SO$_4$. The solvent was removed in vacuo to give the crude product which was purified by column chromatography (silica gel, ethyl acetate) to give the pure 16 (0.4 g, 83%).

R$_f$=0.10 (5% MeOH in ethyl acetate). mp, 138 to 140° C.; [α]$^{23}$$_D$ +14.5 (c 1.05, CHCl$_3$); FTIR (film) ν$_{max}$ 3301, 2949, 2911, 2850, 1723, 1673, 1437, 1371, 1239, 1156, 1008, 689 cm$^{-1}$; $^1$H NMR (CDCl$_3$, 600 MHz): δ 8.48 (1H, br), 6.08 (1H, m), 5.75 (1H, d, J=9.6 Hz), 5.29 (1H, br), 4.13 (1H, d, J=6.6 Hz), 3.83 (3H, m), 3.79 (1H, m), 3.72 (1H, m), 2.84 (1H, d, J=10.2 Hz), 2.20 (1H, m), 2.16 (1H, br), 1.98 (3H, m), 1.77 (3H, m), 1.59 (1H, m), 1.54 (3H, s), 1.25 (1H, m). $^{13}$C NMR (CDCl$_3$, 125 MHz): δ 180.84, 172.95, 135.27, 123.75, 82.00, 80.11, 75.56, 62.39, 53.14, 51.78, 38.95, 28.79, 26.48, 25.04, 20.66, 19.99; HRMS (ESI) calcd. (M+H)$^+$ for C$_{16}$H$_{26}$NO$_6$ 328.1760, found 328.1752.

EXAMPLE 14

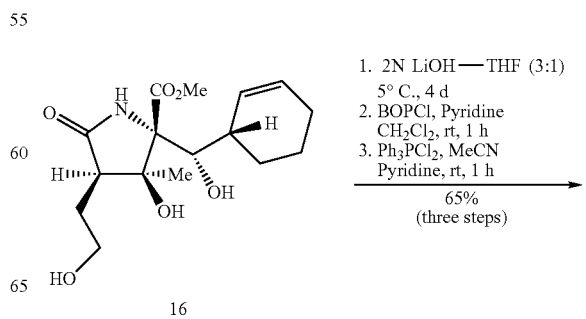

-continued

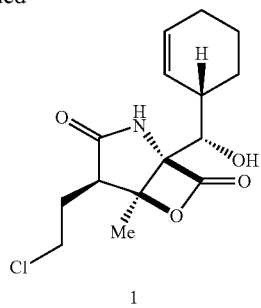

Conversion of (16) to Salinosporamide A (1).

A solution of triol ester 16 (0.164 g, 0.5 mmol) in 3 N aq LiOH (3 mL) and THF (1 mL) was stirred at 5° C. for 4 days until hydrolysis was complete. The acid reaction mixture was acidified with phosphoric acid (to pH 3.5). The solvent was removed in vacuo and the residue was extracted with EtOAc, separated, and concentrated in vacuo to give the crude trihydroxy carboxylic acid 16a (not shown). The crude acid was suspended in dry $CH_2Cl_2$ (2 mL), treated with pyridine (0.5 mL) and stirred vigorously at 23° C. for 5 min. To this solution was added BOPCl (152 mg, 0.6 mmol) at 23° C. under argon, and stirring was continued for 1 h. The solvent was removed under high vacuum and the residue was suspended in dry $CH_3CN$ (1 mL) and treated with pyridine (1 mL). To this solution was added $PPh_3Cl_2$ (333 mg, 1.0 mmol) at 23° C. under argon with stirring. After 1 h the solvent was removed in vacuo. The crude product was purified by column chromatography (silica gel, ethyl acetate-$CH_2Cl_2$, 1:5) to give the pure β-lactone 1 (100 mg, 64%) as a colorless solid.

$R_f$=055 (50% ethyl acetate in hexane). mp, 168-170° C. (authentic sample: 168-170° C., 169-171° C. in Angew. Chem. Int. Ed., 2003, 42, 355-357); mixture mp, 168-170° C. $[α]^{23}_D$ −73.2 (c 0.49, MeOH), −72.9 (c 0.55, MeOH, in Angew. Chem. Int. Ed., 2003, 42, 355-357); FTIR (film) $v_{max}$: 3406, 2955, 2920, 2844, 1823, 1701, 1257, 1076, 1012, 785, 691 cm$^{-1}$; $^1$H NMR (CDCl$_3$, 500 MHz): δ 10.62 (1H, br), 6.42 (1H, d, J=10.5 Hz), 5.88 (1 H, m), 4.25 (1H, d, J=9.0 Hz), 4.14 (1H, m), 4.01 (1H, m), 3.17 (1H, t, J=7.0 Hz), 2.85 (1H, m), 2.48 (1H, m), 2.32 (2H, m), 2.07 (3H, s), 1.91 (2H, m), 1.66 (2H, m), 1.38 (1H, m); $^{13}$C NMR (CDCl$_3$, 125 MHz): δ 176.92, 169.43, 129.08, 128.69, 86.32, 80.35, 70.98, 46.18, 43.28, 39.31, 29.01, 26.47, 25.35, 21.73, 20.00; HRMS (ESI) calcd. for (M−H)$^-$ C$_{15}$H$_{19}$ClNO$_4$ 312.1003, found 312.1003.

EXAMPLE 15

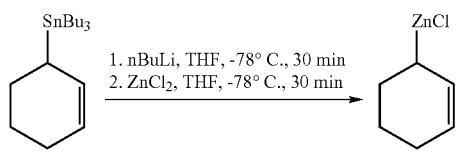

Synthesis of the Cyclohexenyl Zinc Chloride.

To a solution of cyclohexenyltributyl tin (1.85 g 5 mmol) in THF (5 ml) at −78° C. under nitrogen was added nBuLi (2 ml, 2.5M solution in hexane, 5 mmol). See Miyake, H., Yamamura, K., Chem. Lett., 1992, 507-508. After an additional 30 min stirring, ZnCl$_2$ (5 ml, 1 M solution in THF, 5 mmol) was added and stirring was continued at this temperature for 30 min at −78° C. to give a 0.5M solution of 2-cyclohexenyl zinc chloride for reaction with the aldehyde 13.

The present invention has been described in detail, including the preferred embodiments thereof. However, it will be appreciated that those skilled in the art, upon consideration of the present disclosure, may make modifications and/or improvements on this invention and still be within the scope of this invention as set forth in the following claims.

What is claimed is:

1. The synthetic intermediate of Scheme 2, Compound 14, having the structure:

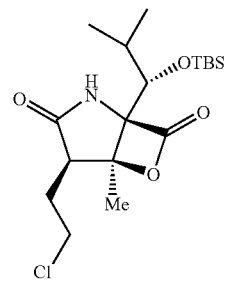

wherein TBS is t-butyldimethylsilyl.

2. The synthetic intermediate of Scheme 3, Compound 29, having the structure:

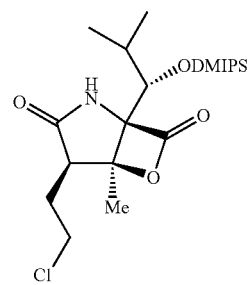

wherein DMIPS is dimethyl isopropyl silyl.

3. The compound having the formula:

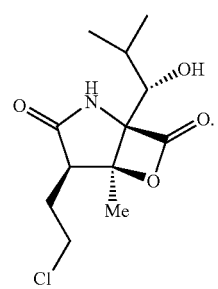

4. Compounds having the Formula Ia:

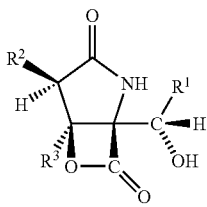

wherein:
- $R^1$ is a substituted C1-C8 alkyl selected from the group consisting of methyl, ethyl, propyl, iso-propyl, n-butyl, iso-butyl, and tert-butyl, each substituted with at least one substituent selected from the group consisting of Cl and F;
- $R^2$ is selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; benzyl and substituted benzyl; wherein the substituent groups are independently selected from the group consisting of C1-C4 alkoxy, amido, halogen and aryl;
- $R^3$ is selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; methylene-C3-C8 cycloalkyl; benzyl and substituted benzyl; wherein the substituent groups are independently selected from the group consisting of C1-C4 alkoxy, amido, and halogen; and
with the proviso that $R^3$ is not methyl when $R^2$ is 2-chloroethyl and $R^1$ is 2-cyclohexenyl.

5. Compounds having the Formula Ia:

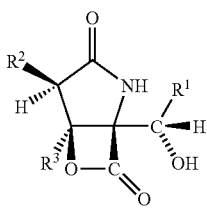

wherein:
- $R^1$ is selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; benzyl and substituted benzyl; wherein the substituent groups are independently selected from the group consisting of C1-C4 alkoxy, amido, and halogen;
- $R^2$ is selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; benzyl and substituted benzyl; wherein the substituent groups are independently selected from the group consisting of C1-C4 alkoxy, amido, halogen and aryl;
- $R^3$ is a substituted C1-C8 alkyl selected from the group consisting of methyl, ethyl, n-propyl, iso-propyl, n-butyl, iso-butyl, and tert-butyl, each substituted with at least one substituent selected from the group consisting of Cl and F; and
with the proviso that $R^3$ is not methyl when $R^2$ is 2-chloroethyl and $R^1$ is 2-cyclohexenyl.

6. Compounds having the Formula IIa:

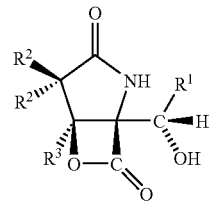

wherein:
- $R^1$ is a substituted C1-C8 alkyl selected from the group consisting of methyl, ethyl, propyl, iso-propyl, n-butyl, iso-butyl, and tert-butyl, each substituted with at least one substituent selected from the group consisting of Cl and F;
- each $R^2$ group is independently selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; benzyl and substituted benzyl; wherein the substituent groups are independently selected from the group consisting of C1-C4 alkoxy, amido, halogen and aryl; or alternatively, the two $R^2$ groups are joined to form the spiro ring group:

$$-CH_2-(CH_2)_n-CH_2-$$

where n has a value selected from 0, 1, 2, 3, or 4; and
- $R^3$ is selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; methylene-C3-C8 cycloalkyl; benzyl and substituted benzyl; wherein the substituent groups are independently selected from the group consisting of C1-C4 alkoxy, amido, and halogen.

7. Compounds having the Formula IIa:

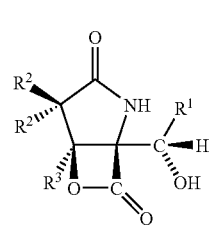

wherein:
- $R^1$ is selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; benzyl and substituted benzyl;

wherein the substituent groups are independently selected from the group consisting of C1-C4 alkoxy, amido, and halogen;

each $R^2$ group is independently selected from the group consisting of substituted or unsubstituted C1-C8 alkyl; substituted or unsubstituted C2-C8 alkenyl; substituted or unsubstituted C2-C8 alkynyl; substituted or unsubstituted, saturated or unsaturated, C3-C8 cycloalkyl; benzyl and substituted benzyl; wherein the substituent groups are independently selected from the group consisting of C1-C4 alkoxy, amido, halogen and aryl; or alternatively, the two $R^2$ groups are joined to form the spiro ring group:

—CH$_2$—(CH$_2$)$_n$—CH$_2$— where n has a value selected from 0, 1, 2, 3, or 4; and $R^3$ is a substituted $C^1$-C8 alkyl selected from the group consisting of methyl, ethyl, n-propyl, iso-propyl, n-butyl, iso-butyl, and tert-butyl, each substituted with at least one substituent selected from the group consisting of Cl and F.

* * * * *